(12) United States Patent
Kim et al.

(10) Patent No.: US 12,172,053 B2
(45) Date of Patent: Dec. 24, 2024

(54) ELECTRONIC APPARATUS AND CONTROL METHOD THEREFOR

(71) Applicant: SAMSUNG ELECTRONICS CO., LTD., Suwon-si (KR)

(72) Inventors: Jongho Kim, Suwon-si (KR); Cheulhee Hahm, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 53 days.

(21) Appl. No.: 18/095,859

(22) Filed: Jan. 11, 2023

(65) Prior Publication Data

US 2023/0166157 A1 Jun. 1, 2023

Related U.S. Application Data

(63) Continuation of application No. PCT/KR2021/011676, filed on Aug. 31, 2021.

(30) Foreign Application Priority Data

Oct. 20, 2020 (KR) ........................ 10-2020-0135661

(51) Int. Cl.
*H04N 23/60* (2023.01)
*A63B 24/00* (2006.01)
(Continued)

(52) U.S. Cl.
CPC ...... *A63B 24/0075* (2013.01); *A63B 71/0622* (2013.01); *G06F 3/013* (2013.01);
(Continued)

(58) Field of Classification Search
None
See application file for complete search history.

(56) References Cited

U.S. PATENT DOCUMENTS

| 11,216,178 B2 | 1/2022 | Choi et al. |
| 2012/0257035 A1 | 10/2012 | Larsen |

(Continued)

FOREIGN PATENT DOCUMENTS

| CN | 104524742 A | 4/2015 |
| JP | 2012-221498 A | 11/2012 |

(Continued)

OTHER PUBLICATIONS

International Search Report dated Dec. 21, 2021, issued by the International Searching Authority in counterpart International Application No. PCT/KR2021/011676 (PCT/ISA/210).

(Continued)

*Primary Examiner* — Eileen M Adams
(74) *Attorney, Agent, or Firm* — Sughrue Mion, PLLC

(57) ABSTRACT

An electronic apparatus includes: a camera; a display; a memory; and a processor configured to: control the display to display a coaching image received from an external server and a user image obtained through the camera; identify a gaze direction of a user based on the obtained user image; based on the gaze direction of the user not being in a threshold range, obtain a feedback image including the coaching image and the user image based on posture information of a first object included in the coaching image and posture information of a second object included in the user image, and store the obtained feedback image in the memory; and control the display to display the stored feedback image.

15 Claims, 22 Drawing Sheets

(51) Int. Cl.
  *A63B 71/06* (2006.01)
  *G06F 3/01* (2006.01)
  *G06T 7/73* (2017.01)
  *H04N 5/77* (2006.01)
(52) U.S. Cl.
  CPC .......... *G06T 7/74* (2017.01); *H04N 5/77* (2013.01); *H04N 23/60* (2023.01); *A63B 2024/0068* (2013.01); *A63B 2071/065* (2013.01); *A63B 2220/05* (2013.01); *A63B 2220/807* (2013.01); *A63B 2230/62* (2013.01); *G06T 2207/10016* (2013.01); *G06T 2207/30201* (2013.01)

(56) References Cited

U.S. PATENT DOCUMENTS

| | | |
|---|---|---|
| 2015/0099252 A1 | 4/2015 | Anderson et al. |
| 2016/0216770 A1 | 7/2016 | Jang et al. |
| 2017/0237986 A1 | 8/2017 | Choi et al. |
| 2018/0211122 A1* | 7/2018 | Amico .............. G06F 18/24 |
| 2020/0012418 A1 | 1/2020 | Choi et al. |
| 2020/0134875 A1* | 4/2020 | Yi .................. G06F 18/28 |
| 2021/0004618 A1* | 1/2021 | Qin ................. B60W 40/08 |

FOREIGN PATENT DOCUMENTS

| | | |
|---|---|---|
| KR | 10-2009-0111574 A | 10/2009 |
| KR | 10-2012-0131342 A | 12/2012 |
| KR | 10-2015-0061476 A | 6/2015 |
| KR | 10-1711488 B1 | 3/2017 |
| KR | 10-2017-0094745 A | 8/2017 |
| KR | 10-1970687 B1 | 4/2019 |
| KR | 10-2097190 B1 | 4/2020 |
| KR | 10-2020-0094915 A | 8/2020 |
| KR | 10-2021-0041968 A | 4/2021 |
| KR | 10-2021-0043174 A | 4/2021 |
| KR | 10-2022-0000435 A | 1/2022 |
| KR | 10-2022-0021581 A | 2/2022 |

OTHER PUBLICATIONS

Written Opinion dated Dec. 21, 2021, issued by the International Searching Authority in counterpart International Application No. PCT/KR2021/011676 (PCT/ISA/237).

Communication issued Nov. 8, 2023 issued by the European Patent Office in European Patent Application No. 21883002.4.

* cited by examiner

FIG. 4
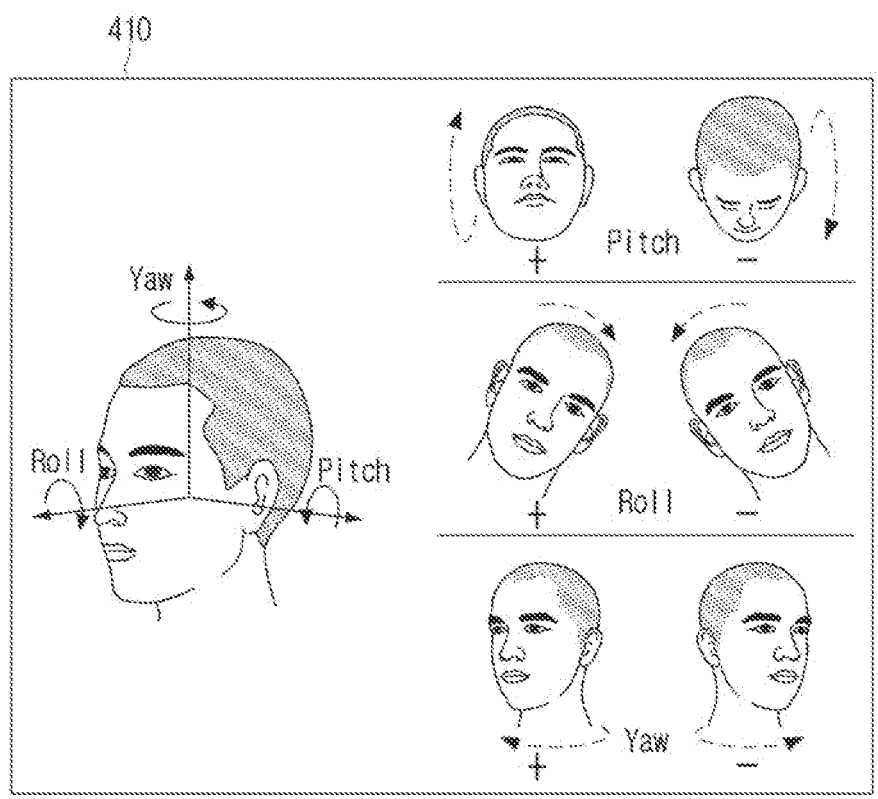
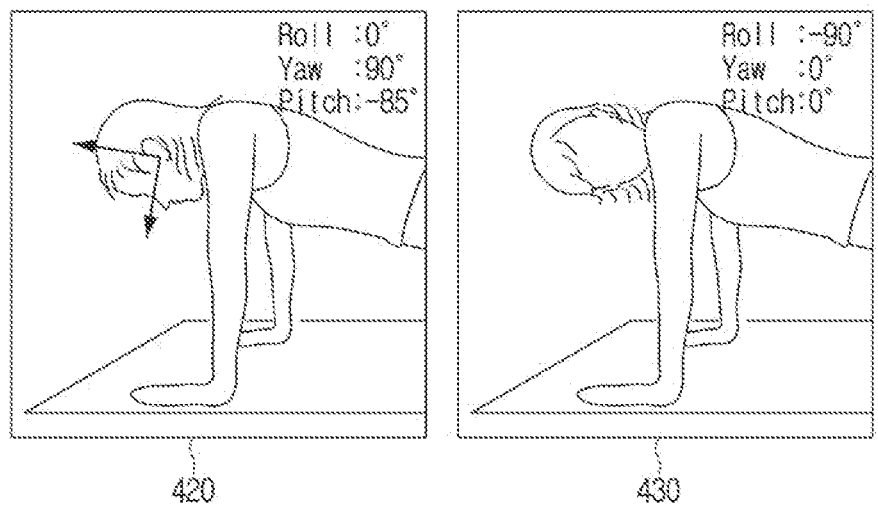

FIG. 8

805
$$DV(1)=E(Vc1,Vu1)$$
$$DV(2)=E(Vc2,Vu2)$$
$$\vdots$$
$$DV(15)=E(Vc15,Vu15)$$

$$DV(total)=wv1*DV(1)+wv2*DV(2)+ \cdots +wv15*DV(15)$$

810
$$DL(1,2)=d(L(Vc1, Vc2), L(Vu1, Vu2))$$
$$DL(1,3)=d(L(Vc1, Vc3), L(Vu1, Vu3))$$
$$\vdots$$
$$DL(14,15)=d(L(Vc14, Vc15), L(Vu14, Vu15))$$

$$DL(total)=wl1*DL(1,2)+wl2*DL(1,3)+ \cdots +wl14*DL(14,15)$$

815
$$DA(1,2-1,3)=C(A(L(Vc1, Vc2), L(Vc1, Vc3)), A(L(Vu1, Vu2), L(Vu1, Vu3)))$$
$$DA(1,2-1,6)=C(A(L(Vc1, Vc2), L(Vc1, Vc6)), A(L(Vu1, Vu2), L(Vu1, Vu6)))$$
$$\vdots$$
$$DA(13,14-14,15)=C(A(L(Vc13, Vc14), L(Vc14, Vc15)), A(L(Vu13, Vu14), L(Vu14, Vu15)))$$

$$DA(total)=wa1*DA(1,2-1,3)+wa2*DA(1,2-1,6)+ \cdots +wa14*DA(13,14-14,15)$$

820
$$D(total)=w1*DV(total)+w2*DL(total)+w3*DA(total)$$

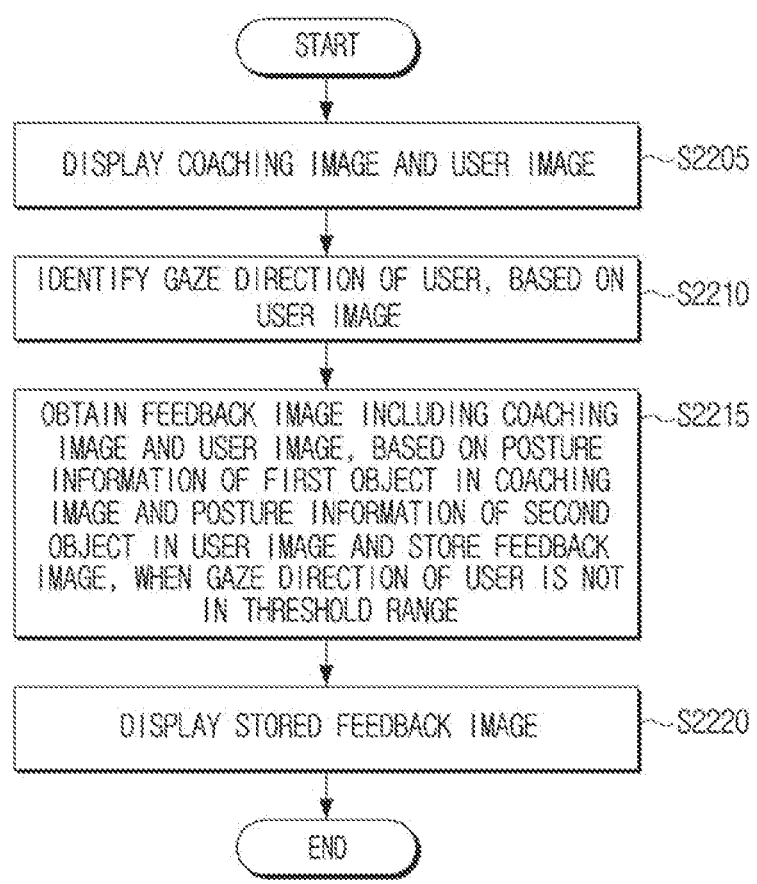

ELECTRONIC APPARATUS AND CONTROL METHOD THEREFOR

CROSS-REFERENCE TO RELATED APPLICATIONS

This application is a by-pass continuation application of International Application No. PCT/KR2021/011676, filed on Aug. 31, 2021, which based on and claims priority to Korean Patent Application No. 10-2020-0135661, filed on Oct. 20, 2020, in the Korean Intellectual Property Office, the disclosures of which are incorporated by reference herein in their entireties.

BACKGROUND

1. Field

The disclosure relates to an electronic apparatus for comparing and analyzing different images and a control method thereof, and more particularly, to an electronic apparatus for comparing and analyzing motions in a coaching image and a user image and provides feedback, and a control method thereof.

2. Description of Related Art

Generally, home training is designed to allow ordinary users to exercise while watching an exercise video. When home training is performed through a display device, a user who is performing home training may be photographed by a camera connected to the display device. When images of the user's exercise are recorded, the user can correct or analyze their posture using the recorded images. For example, the user may correct their wrong posture using the recorded images.

However, when all images of the user are recorded, the amount of recorded data increases and thus all of the images should be viewed from the beginning unnecessarily. It may be difficult for the user to accurately imitate a posture when the user's eyes are not directed to an electronic apparatus while watching coaching or guidance images of the exercise video. Alternatively or additionally, when the user makes a motion while looking ahead to watch the expert's motion made while looking at a side in the coaching image, the user would feel that their motion is different from the expert's motion.

SUMMARY

Provided are an electronic apparatus for obtaining a feedback image including a coaching image and a user image by taking into account a gaze direction of a user, and a control method thereof.

According to an aspect of the disclosure, an electronic apparatus includes: a camera; a display; a memory; and a processor configured to: control the display to display a coaching image received from an external server and a user image obtained through the camera; identify a gaze direction of a user based on the obtained user image; based on the gaze direction of the user not being in a threshold range, obtain a feedback image including the coaching image and the user image based on posture information of a first object included in the coaching image and posture information of a second object included in the user image, and store the obtained feedback image in the memory; and control the display to display the stored feedback image.

The processor may be further configured to: obtain a similarity between the posture information of the first object and the posture information of the second object; and based on the obtained similarity being less than a threshold, obtain the feedback image including the coaching image and the user image.

The processor may be further configured to: obtain first skeleton data corresponding to the first object based on the obtained coaching image; obtain second skeleton data corresponding to the second object on the obtained user image; and obtain a similarity between the posture information of the first object and the posture information of the second object based on a difference between the first skeleton data and the second skeleton data.

Each of the first skeleton data and the second skeleton data may include vertex coordinate information, length information of connection lines connecting two adjacent vertices, and angle information between two adjacent connection lines, and the processor may be further configured to obtain the difference between the first skeleton data and the second skeleton data based on the vertex coordinate information, the length information of the connection lines, and the angle information.

The processor may be further configured to: apply a first weight group to differences between the vertex coordinate information included in the first skeleton data and the vertex coordinate information included in the second skeleton data, and obtain a first sum of the differences to which the first weight group is applied; apply a second weight group to differences between the length information of the connection lines included in the first skeleton data and the length information of the connection lines included in the second skeleton data, and obtain a second sum of the differences to which the second weight group is applied; apply a third weight group to differences between the angle information included in the first skeleton data and the angle information included in the second skeleton data, and obtain a third sum of the differences to which the third weight group is applied; and obtain the difference between the first skeleton data and the second skeleton data based on the first sum, the second sum, and the third sum.

The first weight group, the second weight group, and the third weight group may include different weights.

The processor may be further configured to determine weights included in each of the first weight group, the second weight group, and the third weight group based on the posture information of the first object.

The processor may be further configured to: based on the posture information of the first object being identified as a predetermined posture, store, as a first video, feedback images from a time point at which generation of the feedback images begins to a first time point at which the predetermined posture is identified; and based on a subsequent posture of the identified first object being identified again as the predetermined posture, store, as a second video, feedback images from the first time point to a second time point at which the predetermined posture is identified again.

The processor may be further configured to: identify a sub-region in which a difference between the posture information of the first object and the posture information of the second object is greater than or equal to a threshold; obtain a sub-image of the coaching image and a sub-image of the user image by changing sizes of the first object and the second object that are included in the identified sub-region; and generate a feedback image including the coaching image, the user image, the sub-image of the coaching image, and the sub-image of the user image.

The processor may be further configured to: identify a face region corresponding to the second object included in the user image; obtain a face rotation angle based on the identified face region; and identify the gaze direction of the user based on the face rotation angle.

According to an aspect of the disclosure, a method performed by an electronic apparatus, includes: displaying a coaching image and a user image; identifying a gaze direction of a user based on the user image; based on the gaze direction of the user not being in a threshold range, obtaining a feedback image including the coaching image and the user image based on posture information of a first object included in the coaching image and posture information of a second object included in the user image, and storing the obtained feedback image; and displaying the stored feedback image.

The method may further include: obtaining a similarity between the posture information of the first object and the posture information of the second object; and based on the obtained similarity being less than a threshold, obtaining the feedback image including the coaching image and the user image.

The obtaining the similarity may include: obtaining first skeleton data corresponding to the first object based on the obtained coaching image; obtaining second skeleton data corresponding to the second object on the obtained user image; and obtaining a similarity between the posture information of the first object and the posture information of the second object based on a difference between the first skeleton data and the second skeleton data.

Each of the first skeleton data and the second skeleton data may include vertex coordinate information, length information of connection lines connecting two adjacent vertices, and angle information between two adjacent connection lines, and the obtaining the similarity may include obtaining the difference between the first skeleton data and the second skeleton data based on the vertex coordinate information, the length information of the connection lines, and the angle information.

The obtaining the similarity may further include: applying a first weight group to differences between the vertex coordinate information included in the first skeleton data and the vertex coordinate information included in the second skeleton data, and obtaining a first sum of the differences to which the first weight group is applied; applying a second weight group to differences between the length information of the connection lines included in the first skeleton data and the length information of the connection lines included in the second skeleton data, and obtaining a second sum of the differences to which the second weight group is applied; applying a third weight group to differences between the angle information included in the first skeleton data and the angle information included in the second skeleton data, and obtaining a third sum of the differences to which the third weight group is applied; and obtaining the difference between the first skeleton data and the second skeleton data based on the first sum, the second sum, and the third sum.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 4 is a diagram for describing analyzing a gaze direction of a user;

FIG. 8 is a diagram for describing a process of obtaining a similarity between pieces of posture information based on skeleton data;

FIG. 19 is a diagram for describing providing a notification message for changing a location of a user;

FIG. 22 is a diagram for describing a method of an electronic apparatus according to an embodiment of the disclosure.

DETAILED DESCRIPTION

Hereinafter, the disclosure will be described in detail with reference to the accompanying drawings.

In embodiments of the disclosure, general terms that have been widely used nowadays are selected, if possible, in consideration of functions of the disclosure, but non-general terms may be selected according to the intentions of technicians in the art, precedents, or new technologies, etc. Some terms may be arbitrarily chosen by the present applicant, and in this case, the meanings of these terms will be explained in corresponding parts of the disclosure in detail. Accordingly, the terms used herein should be defined not based on the names thereof but based on the meanings thereof and the whole context of the disclosure.

As used herein, expressions such as "have", "may have," "include" or "may include" are intended to indicate the presence of features (e.g., a numerical value, a function, an operation, a component of a machine part, etc.) and do not exclude the presence of additional features.

It should be understood that the expression "at least one of A and/or B" indicates only "A", only "B", or both of "A and B".

As used herein, the terms "first," "second," and the like may be used to describe various elements regardless of order and/or importance and distinguish one element from another element, but these elements should not be limited by these terms.

When an element (e.g., a first element) is referred to as being "operatively or communicatively coupled with/to" or "connected to" another element (e.g., a second element), the element should be understood as being directly connected to the other element or connected to the other element via another element (e.g., a third element).

As used herein, the singular expressions are intended to include plural forms as well, unless the context clearly dictates otherwise. It will further be understood that the terms "comprise" and/or "comprising", when used herein, specify the presence of stated features, integers, steps, operations, elements, components, or a combination thereof, but do not preclude the presence or addition of one or more features, integers, steps, operations, elements, components, or a combination thereof.

In the disclosure, the term "module" or "unit" may refer to an element performing at least one function or operation, and may be embodied as hardware, software, or a combination thereof. A plurality of "modules" or a plurality of "units" may be integrated into at least one module to form at least one processor, except a "module" or "unit" which need be embodied as particular hardware.

As used herein, the term "user" may refer to a person or a device (e.g., an artificial intelligence electronic device) capable of using an electronic device.

An embodiment of the disclosure will now be described in more detail with reference to the accompanying drawings.

Figure 1:
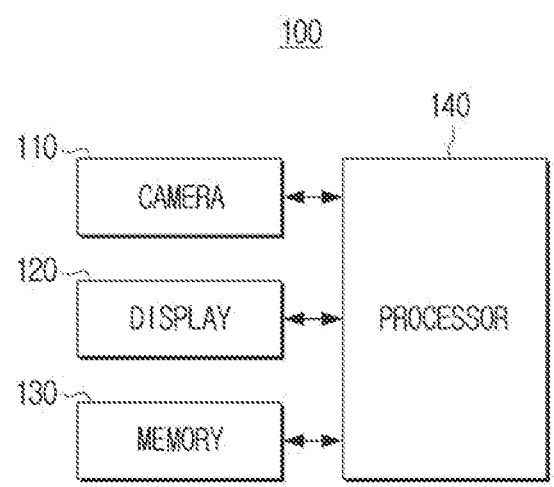
FIG. 1 is a block diagram of an electronic apparatus according to an embodiment of the disclosure.

FIG. 1 is a block diagram of an electronic apparatus according to an embodiment of the disclosure. Referring to FIG. 1, an electronic apparatus 100 may include a camera 110, a display 120, a memory 130, and a processor 140.

According to one or more embodiments of the disclosure, the electronic apparatus 100 may include, for example, at least one of a smart phone, a tablet PC, a cellular phone, a desktop PC, a laptop PC, a personal digital assistant (PDA), or a portable multimedia player (PMP). In some embodiments, the electronic apparatus 100 may include, for example, at least one of a television, a digital video disk (DVD) player, or a media box (e.g., Samsung HomeSync™, Apple TV™, or Google TV™).

The camera 110 is configured to capture an image of a subject, and the captured image is a concept including both a moving image and a still image. The camera 110 may obtain an image of at least one external device and be implemented as a camera, a lens, an infrared sensor, or the like.

The camera 110 may include a lens and an image sensor. A type of the lens may be a general-purpose lens, a wide-angle lens, a zoom lens, or the like, and may be determined according to the type, features, and use environment of the electronic apparatus 100. A complementary metal oxide semiconductor (CMOS), a charge-coupled device (CCD) or the like may be used as the image sensor.

The camera 110 outputs light incident thereon in the form of an image signal. Specifically, the camera 110 may include a lens, pixels, and an analog-to-digital (AD) converter. The lens collects light from the subject and forms an optical image on an imaging area, and the pixels may output light incident on the lens in the form of an analog image signal. The AD converter may convert an analog image signal into a digital image signal and output the digital image signal. In particular, the camera 110 may be arranged to perform photographing in a direction toward a front surface of the electronic apparatus 100 and thus may capture an image of a user located in front of the electronic apparatus 100 to obtain the captured image.

The display 120 may be embodied as various types of displays such as a liquid crystal display (LCD), an organic light-emitting diode (OLED) display, and a plasma display panel (PDP). A driving circuit, a backlight unit, etc., which are in the form of a a-silicon thin-film transistor (TFT), a low-temperature polysilicon (LTPS) TFT, or an organic TFT (OTFT), may be included in the display 120. The display 120 may be embodied as a touch screen combined with a touch sensor, a flexible display, a three-dimensional (3D) display, or the like.

According to an embodiment of the disclosure, the display 120 may include not only a display panel configured to an image but also a bezel housing the display panel. In particular, according to an embodiment of the disclosure, the bezel may include a touch sensor for sensing a user interaction.

The memory 130 may be implemented as an internal memory, such as a read-only memory (ROM) (e.g., electrically erasable programmable ROM) or a random access memory (RAM) included in the processor 140, or a memory separate from the processor 140. In this case, the memory 130 may be embodied as a memory embedded in the electronic apparatus 100 or a memory detachable from the electronic apparatus 100 according to a purpose of storing data. For example, data for driving the electronic apparatus 100 may be stored in the memory embedded in the electronic apparatus 100, and data for expanding the electronic apparatus 100 may be stored in the memory detachable from the electronic apparatus 100.

The processor 140 may control overall operations of the electronic apparatus 100. Specifically, the processor 140 performs a function of controlling the overall operations of the electronic apparatus 100.

The processor 140 may be embodied as a digital signal processor (DSP) configured to process a digital signal, a microprocessor, or a time controller (TCON). However, the processor 140 is not limited thereto, and may include or be referred to as at least one of a central processing unit (CPU), a microcontroller unit (MCU), a micro-processing unit (MPU), a controller, an application processor (AP), a graphics-processing unit (GPU), a communication processor (CP), or an ARM processor. Alternatively, the processor 140 may be embodied as a system-on-chip (SoC) storing a processing algorithm, a large-scale integrated (LSI) circuit, or a field programmable gate array (FPGA). Alternatively or additionally, the processor 140 may execute computer executable instructions stored in the memory to perform various functions.

The processor 140 may control the display 120 to display a coaching image received from an external server and a user image (i.e., an image of a user) obtained by the camera 110, identify a gaze direction of a user based on the obtained user image, obtain a feedback image including the coaching image and the user image based on posture information of a first object included in the coaching image and posture information of a second object included in the user image, when the gaze direction of the use is not in a threshold range, store the obtained feedback image in the memory 130, and control the display 120 to display the stored feedback image.

The coaching image may be understood as an expert's image for home training. For example, the coaching image may be a lecture image related to various types of exercises (stretching, yoga, Pilates, and sports games). The processor 140 may receive a coaching image from an external server. The external server may be a content provider. The content provider may be understood as a broadcast channel that supplies broadcast content, an Internet Protocol Television (IPTV) operator that provides specific content, or an Internet server that provides specific content. The processor 140 may receive a coaching image in real time from an external server and directly display the coaching image on the display 120. According to another embodiment, the processor 140 may display a coaching image stored in the memory 130 on the display 120.

The processor 140 may photograph a user through the camera 110. The processor 140 may obtain a user image as a result of photographing the user. Alternatively or additionally, the processor 140 may display the obtained user image on the display 120 in real time.

The processor 140 may identify a gaze direction of the user. The processor 140 may analyze the obtained user image to identify a human object. The human object may include a character image as well as an image of a human. The human object may be understood as a human-shaped object. The processor 140 may also identify a human object in the coaching image. A human object obtained from the coaching image will be referred to as a first object, and a human object obtained from the user image will be referred to as a second object.

The processor 140 may identify a face region corresponding to the second object included in the user image, obtain a face rotation angle based on the identified face region, and identify a gaze direction of the user based on the face rotation angle.

The processor 140 may identify a human object in the user image and identify a face region of the identified human object. Alternatively or additionally, the processor 140 may identify the gaze direction of the user in the identified face region. The processor 140 may identify the gaze direction of the user by a head pose estimation technique.

The processor 140 may identify whether the gaze direction of the user is within a threshold range. The threshold range may be understood as a predetermined angle. The predetermined angle may be an angle at which the user's eyes are not directed toward the electronic apparatus 100. When a roll, a yaw, and a pitch, which are rotation angles in a 3D space, are used, the threshold range may be $\{-90°<\text{Roll}<+90°$ and $-60°<\text{Yaw}<+60°$ and $-45°<\text{Pitch}<+45°\}$. Thus, when it is identified that the roll, the yaw and the pitch are in the threshold range, the processor 140 may identify that the gaze direction of the user is directed to the electronic apparatus 100. When it is identified that the user gaze direction is directed to the electronic apparatus 100, the processor 140 may continuously display the coaching image and the user image on the display 120 without generating a feedback image.

Conversely, when it is identified that the roll, the yaw and the pitch are not in the threshold range, the processor 140 may identify that the gaze direction of the user is not directed to the electronic apparatus 100. When it is identified that the user gaze direction is not directed to the electronic apparatus 100, the processor 140 may generate a feedback image including the coaching image and the user image based on the posture information of the first object included in the coaching image and the posture information of the second object included in the user image. The processor 140 may store the generated feedback image in the memory 130. Alternatively or additionally, the processor 140 may display the feedback image stored in the memory 130 on the display 120 based on a user input.

The feedback image may be an analysis image for comparing the coaching image and the user image with each other. Accordingly, the feedback image may be reproduced upon a separate request from the user after the coaching image is watched. In simply displaying the coaching image and the user image in a screen image on the display 120, the screen image may not be referred to as a feedback image to avoid confusion. To distinguish between simply displaying the coaching image and the user image in a screen image and generating a new image including the coaching image and the user image, an image in the displaying of the coaching image and the user image may be referred to as a mixture of images (combined image or mixed image) and an image in the generating of the new image may be referred to as a feedback image. The feedback image may be also referred to as a service image, a comparison image, a comparison analysis image, a recorded image or the like, as well as an analysis image.

In order to generate the feedback image, the processor 140 may additionally take into account the posture information of the first object and the posture information of the second object included in the user image.

The processor 140 may obtain a similarity between the posture information of the first object and the posture information of the second object, and obtain the feedback image including the coaching image and the user image when the similarity is less than a threshold.

The posture information of the first object and the posture information of the second object may each include skeleton data, and the skeleton data may be information indicating a posture of the first or second object. Alternatively or additionally, the processor 140 may obtain a similarity to identify the similarity between the posture information of the first object and the posture information of the second object. The similarity may be obtained based on the skeleton data. When the similarity is high, the processor 140 may identify that the posture of the first object and the posture of the second object are the same. In contrast, when the similarity is low, the processor 140 may identify that the posture of the first object and the posture of the second object are different from each other.

The feedback image is aimed to give feedback on a wrong posture when a user cannot accurately imitate a motion according to the coaching image. Accordingly, when the similarity is less than a threshold, the processor 140 may generate a feedback image including a coaching image and a user image displayed at a point in time when the similarity is less than the threshold.

The processor 140 may obtain first skeleton data corresponding to a first object based on an obtained coaching image, obtain second skeleton data corresponding to a second object based on an obtained user image, and obtain a similarity between posture information of the first object and posture information of the second object based on a difference between the first skeleton data and the second skeleton data.

The first skeleton data and the second skeleton data may include vertex coordinate information, length information of connection lines connecting two adjacent vertices, and angle information between two adjacent connection lines, and the processor 140 may obtain a difference between the first skeleton data and the second skeleton data based on the vertex coordinate information, the length information, and the angle information.

Objects between which a difference is calculated are not arbitrary objects, and a predetermined method may be included in the skeleton data. Specifically, objects between which a difference is calculated may be determined based on a part the body of the object. The part of the body may include at least one of a neck, a head, a shoulder, an elbow, a wrist, an abdomen, a waist, a knee, or an ankle.

For example, the processor 140 may identify fifteen vertices in the coaching image based on a part of the body of the first object. Alternatively or additionally, the processor 140 may identify fifteen vertices in the user image based on a part of the body of the second object. The fifteen vertices obtained in each of the coaching image and the user image may be assigned identification numbers, based on the positions of the parts of the body. For example, a position corresponding to the neck may be a first vertex and a position corresponding to the face may be a second vertex. Objects between which a difference is calculated may be the first vertex in the coaching image and the first vertex in the user image. That is, the processor 140 may compare vertices, which correspond to the same part of the body in the coaching image and the user image, with each other. The comparing of the vertices is performed to compare a certain location on the body in the coaching image with a certain location on the body in the user image. That is, the processor 140 may identify vertices corresponding to the same part of the body (or the location of the part of the body) in the coaching image and the user image, and obtain a difference between the vertices identified in the coaching image and the user image.

As another example, the processor 140 may identify connection lines corresponding to the same part of the body (or a location of the part of the body) in the coaching image and the user image, and obtain a difference between the connection lines identified in the coaching image and the user image. The difference between the connection lines may be obtained using at least one of length information or inclination information.

As another example, the processor 140 may identify angles corresponding to the same parts of the bodies (or locations of the parts) in the coaching image and the user image, and obtain a difference between the angles identified in the coaching image and the user image.

The vertices, the connection lines, and the angles will be described in detail with reference to FIGS. 5 and 6 below.

The processor 140 may apply a first weight group to differences between vertex coordinate information in first skeleton data and vertex coordinate information in second skeleton data, obtain a first sum of the differences to which weights are applied, apply a second weight group to differences between length information of connection lines in the first skeleton data and length information of connection lines in the second skeleton data, obtain a second sum of the differences to which weights are applied, apply a third weight group to differences between angle information in the first skeleton data and angle information in the second skeleton data, obtain a third sum of the differences to which weights are applied, and obtain a difference between the first skeleton data and the second skeleton data based on the first to third sums.

The first weight group, the second weight group, and the third weight group may include different weights.

The obtaining of the difference between the first skeleton data and the second skeleton data based on the first to third sums will be described in detail with reference to FIGS. 7 and 8 below.

The first weight group may include a plurality of weights to be applied to differences between coordinates of vertices identified in the coaching image and coordinates of vertices identified in the user image. The second weight group may include a plurality of weights to be applied to differences between the lengths of connection lines identified in the coaching image and lengths of connection lines identified in the user image. The third weight group may include a plurality of weights to be applied to differences between angles identified in the coaching image and angles identified in the user image. Objects to which the first to third weight groups are applied are different from one another and thus the first to third weight groups may include different weights.

The processor 140 may determine weights included in the first weight group, the second weight group, and the third weight group based on the posture information of the first object.

The weights included in each of these groups may be determined as different weights according to parts of the body.

The first weight group applied to vertices may include fifteen weights. For example, a weight wv1 may be applied to a first vertex corresponding to the neck, and a weight wv2 may be applied to a second vertex corresponding to the face. Weights wv1 and wv2 when the posture information of the first object is a first posture may be different from those when the posture information of the first object is a second posture. This is because a part of the body to be changed largely may vary according to a posture. Accordingly, the processor 140 may change weights differently according to posture information for accurate comparison and analysis. In order to change weights differently according to the posture information, weight information according to the posture information may be previously stored in the memory 130. Alternatively, the weights wv1 and wv2 may vary even for the same posture.

The processor 140 may store, as a first video, feedback images from a point in time when generation of the feedback images begins to a first point in time when a predetermined posture is identified, when the posture information of the first object is identified as the predetermined posture, and store, as a second video, feedback images from the first point in time to a second point in time when the predetermined posture is identified again, when a subsequent posture of the identified first object is identified again as the predetermined posture.

The predetermined posture may be understood as a posture identified before a new posture is taken. For example, in the coaching image, an expert may take the predetermined posture at a point in time when the first posture is switched to the second posture. The predetermined posture may be a basic posture and may be understood as an attention posture or a bowing posture.

Feedback images may be stored in the form of a plurality of videos based on various predetermined events, in addition to the posture information. This will be described in detail with reference to FIGS. 17 and 18 below.

The processor 140 may identify a sub-region in which a difference between the posture information of the first object and the posture information of the second object is greater than or equal to a threshold, obtain a sub-image of the coaching image and a sub-image of the user image by changing the sizes of the first object and the second object in the identified sub-region, and generate a feedback image including all the coaching images and all the user images and the sub-images of the coaching image and the user image.

The sub-image will be described in detail with reference to FIG. 12 below.

The electronic apparatus 100 according to an embodiment of the disclosure may analyze a coaching image and a user image to compare postures of human objects therein (a first object in the coaching image and a second object in the user image) with each other. The electronic apparatus 100 may identify a similarity between postures of the first object and the second object. The electronic apparatus 100 does not determine a posture similarity at every moment that the coaching image is reproduced but may determine a posture similarity only when a gaze direction of the second object is not directed to the electronic apparatus 100. When the gaze direction is directed to the electronic apparatus 100, the electronic apparatus 100 may determine that a difference between postures is easily recognizable even when the posture similarity is low.

Accordingly, the electronic apparatus 100 may determine a posture similarity only when a gaze direction of a user is not directed to the electronic apparatus 100. Accordingly, the electronic apparatus 100 may reduce the number of objects between which a posture similarity is determined, thereby reducing a data throughput or a data processing time. Alternatively or additionally, when a feedback image is generated in consideration of a user's gaze, the size (or amount) of the feedback image may decrease. Due to the decrease of the amount of the feedback image, the electronic apparatus 100 may efficiently use a memory storage space and easily transmit the feedback image to the user's terminal.

It has been described above that the above described various operations are performed by the processor 140. According to an embodiment, the processor 140 may include an image reproduction module, a user gaze detection module, a motion comparator, an image storage, and a feedback image reproduction module, and operations of these modules may be performed separately.

In a coaching image, an expert takes a posture while looking at a side and a user takes a posture while looking straight ahead to watch the coaching image. In a general comparison operation, these operations are likely to be determined to be different operations. When a feedback image is generated to include the operations, most of images may be recorded. However, the electronic apparatus 100 of the disclosure may record images only when a user's gaze is not in a threshold range and thus the amount of images to be recorded may decrease.

Although only a simple configuration of the electronic apparatus 100 is illustrated and described above, various other components may be additionally provided when the electronic apparatus 100 is implemented. This will be described with reference to FIG. 2 below.

Figure 2:
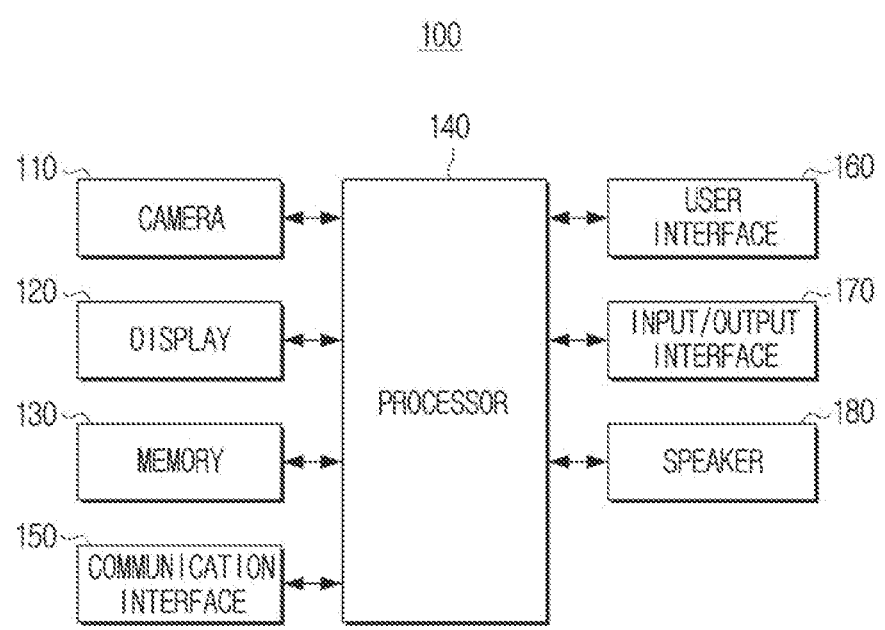
FIG. 2 is a detailed block diagram for describing a configuration of the electronic apparatus of FIG. 1.

FIG. 2 is a detailed block diagram for describing a configuration of the electronic apparatus of FIG. 1. In FIG. 2, the electronic apparatus 100 may include a camera 110, a display 120, a memory 130, a processor 140, a communication interface 150, a user interface 160, an input/output interface 170 and a speaker 180. Operations of the camera 110, the display 120, the memory 130, and the processor 140 that are the same as those described above will not be redundantly described here.

The communication interface 150 is configured to communicate with various types of external devices according to various communication methods. Examples of the communication interface 150 may include a Wi-Fi module, a Bluetooth module, an infrared communication module, a wireless communication module, etc. The Wi-Fi module establishes communication by a WiFi method and the Bluetooth module establishes communication by a Bluetooth method. The wireless communication module may include at least one communication chip for establishing communication according to various wireless communication standards such as ZigBee, 3rd Generation (3G), 3rd Generation Partnership Project (3GPP), LTE Advanced (LTE-A), 4th Generation (4G), and 5th Generation (5G), in addition to the communication methods described above.

The user interface 160 may be embodied as a button, a touch pad, a mouse, a keyboard or the like or as a touch screen for performing both a display function and a manipulation input function as described above. The button may include various types of buttons, such as mechanical buttons, a touch pad, and wheels, which are provided on a certain region such as a front part, a side part, and a rear part of the exterior of the main body of the electronic apparatus 100.

The input/output interface 170 may be a high-definition multimedia interface (HDMI), mobile high-definition link (MHL), universal serial bus (USB), a display port (DP), thunderbolt, a video graphics array (VGA) port, an RGB port, D-subminiature (D-SUB), or digital visual interface (DVI). At least one of an audio signal or a video signal may be input to or output from the input/output interface 170.

In an embodiment, the input/output interface 170 may include a port for inputting or outputting only audio signals and a port for inputting or outputting only video signals as separate ports or may be implemented as one port for inputting or outputting both audio and video signals.

The electronic apparatus 100 may include the speaker 180. The speaker 180 may be a component configured to output not only various types of audio data processed by the input/output interface 170 but also various types of notification sound or voice messages.

The electronic apparatus 100 may further include a microphone. The microphone is a component configured to receive a user's voice or another type of sound and convert the user's voice or the other type of sound into audio data.

The microphone may receive a user's voice in an activated state. For example, the microphone may be integrally formed with an upper, front, or lateral side of the electronic apparatus 100. The microphone may include various types of components, such as a microphone for collecting a user's voice in an analog form, an amplifier circuit for amplifying the collected user's voice, an A/D conversion circuit for sampling the amplified user's voice and converting a result of the sampling into a digital signal, and a filter circuit for removing noise components from the digital signal.

Figure 3:
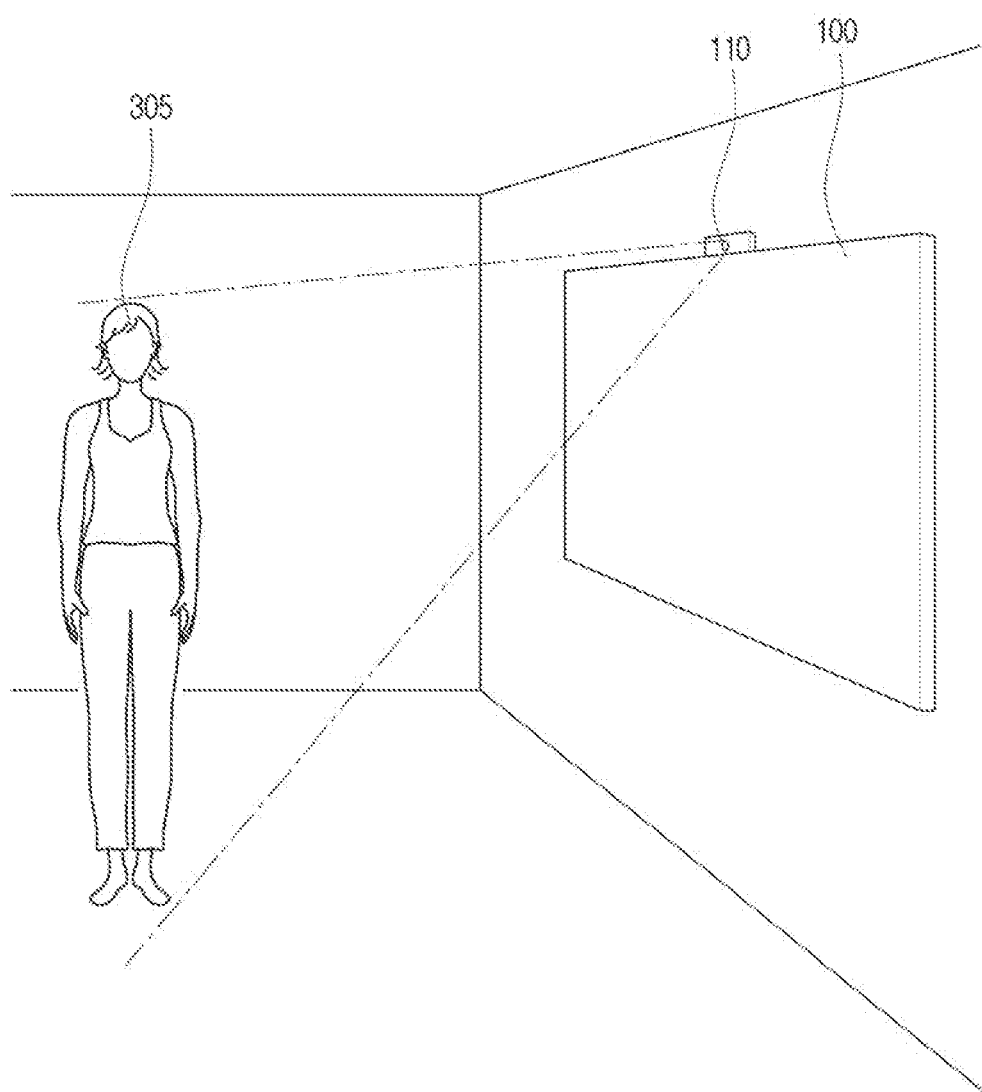
FIG. 3 is a diagram for describing photographing a user by an electronic apparatus.

FIG. 3 is a diagram for describing photographing a user by an electronic apparatus. In FIG. 3, an electronic apparatus 100 may include a camera 110, and the electronic apparatus 100 may photograph a user 305 through the camera 110. Alternatively or additionally, the electronic apparatus 100 may obtain a captured image corresponding to the user 305 through the camera 110. The electronic apparatus 100 may generate a user image by capturing images of the user 305 in real time.

The electronic apparatus 100 may display the generated user image on the display 120 of the electronic apparatus 100. The electronic apparatus 100 may control the display 120 to display the user image together with a coaching image received from an external server.

FIG. 4 is a diagram for describing analyzing a gaze direction of a user. In FIG. 4, an electronic apparatus 100 may identify (or determine) a gaze direction of a user by a head pose estimation technique. Specifically, the processor 140 may use a roll, a yaw and a pitch, which are rotational angles in a 3D space.

According to a first embodiment 410, the roll, the yaw, and the pitch for determining the gaze direction of the user are defined. The roll may be understood as an angel of rotation about a longitudinal axis. The yaw may be understood as an angle of rotation about a vertical axis. The pitch may be understood as an angle of rotation about a lateral axis.

According to a second embodiment 420, the user is doing push-ups while turning their face down. The electronic apparatus 100 may capture images of the user by the camera 110 and obtain a user image. The electronic apparatus 100 may identify a face region of the user in the user image. Alternatively or additionally, the electronic apparatus 100 may identify an angle of rotation of the user's face object based on the identified face region. When the user is turning their face down, the electronic apparatus 100 may obtain face rotation angle data including a roll of 0 degrees, a yaw of 90 degrees, and a pitch of −85 degrees. The electronic apparatus 100 may determine that a gaze direction of the user is not directed to the electronic apparatus 100 (or the camera 110), based on the obtained data.

According to a third embodiment 430, the user is doing push-ups while turning their face toward the electronic apparatus 100. The electronic apparatus 100 may identify an angle of rotation of a user face object based on a user image. When the user is turning their face toward the electronic apparatus 100, the electronic apparatus 100 may obtain face rotation angle data including a roll of −90 degrees, a yaw of 0 degrees, and a pitch of 0 degrees. The electronic apparatus 100 may determine that a gaze direction of the user is directed to the electronic apparatus 100 (or the camera 110), based on the obtained data.

For example, it is determined that the user is looking ahead, i.e., the user is looking at a screen, when a 3D angle of rotation of the face detected in the user image is (Roll, Yaw, Pitch)=(0°, 0°, 0°). It is determined that the user is looking at the electronic apparatus 100, when the 3D angle of rotation is {−90°<Roll<+90° and −60°<Yaw<+60° and −45°<Pitch<+45°}.

Figure 5:
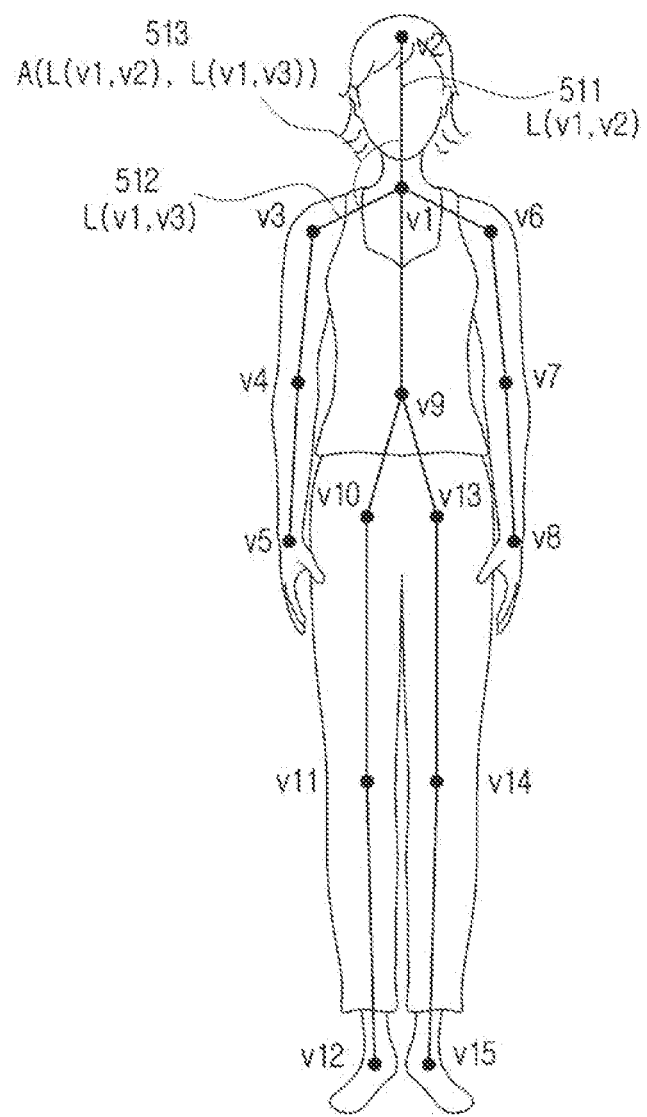
FIG. 5 is a diagram for describing skeleton data of an object.

FIG. 5 is a diagram for describing skeleton data of an object. In FIG. 5, the electronic apparatus 100 may identify a human object 505 in each of a coaching image and a user image. Alternatively or additionally, skeleton data may be obtained based on the identified human object 505. The skeleton data may be understood as data corresponding to joints and major parts of a human, and may be expressed as skeleton.

As the skeleton data, vertex coordinate information, length information of connection lines, and angle information between connection lines. The connection lines may be referred to as edges.

The vertex coordinate information may be understood as points of predetermined parts forming a skeleton of a human object. The number of vertices may be determined in advance according to user settings. In one or more embodiments of the disclosure, there are fifteen vertices. A human object 505 may be provided with vertices v1 to v15. Specifically, v1 may denote the position of the neck, v2 may denote the position of the head, v3 and v6 may denote the positions of the shoulders, v4 and v7 may denote the positions of elbows, v5 and v8 may denote the positions of wrists, v9 may denote a central location on the abdomen, v10 and v13 may denote the positions of two parts of the pelvis, v11 and v14 may denote the positions of the knees, and v12 and v15 may denote the positions of the ankles.

Each of the connection lines may be understood as a line connecting two predetermined vertices among a plurality of vertices. The two vertices may be determined in a predetermined manner. To form a human skeleton, pairs of two vertices may be v1-v2, v1-v3, v3-v4, v4-v5, v1-v6, v6-v7, v7-v8, v1-v9, v9-v10, v10-v11, v11-v12, v9-v13, v13-v14, and v14-v15. Connection lines formed by the pairs of two vertices may be expressed as L(v1,v2) (511), L(v1,v3) (512), L(v3,v4), L(v4,v5), L(v1,v6), L(v6,v7), L(v7,v8), L(v1,v9), L(v9,v10), L(v10,v11), L(v11,v12), L(v9,v13), L(v13,v14), and L(v14,v15). The electronic apparatus 100 may obtain length information of each of the connection lines.

The angle information between connection lines may be understood as an angle between two predetermined connection lines among a plurality of connection lines. The angle information: may be expressed as A(L(v1,v2), L(v1,v3)) (513), A(L(v1,v3)), L(v3,v4), A(L(v3,v4), L(v4,v5)), A(L (v1,v2), L(v1,v6)), A(L(v1,v6), L(v6,v7)), A(L(v6,v7), L(v7,v8)), A(L(v1,v3), L(v1,v9)), A(L(v1,v9), L(v9,v10)), A(L(v9,v10), L(v10,v11)), A(L(v10,v11), L(v11,v12)), A(L (v1,v6), L(v1,v9)), A(L(v1,v9), L(v9,v13)), A(L(v9,v13), L(v13,v14)), A(L(v13,v14), L(v14,v15)).

Figure 6:
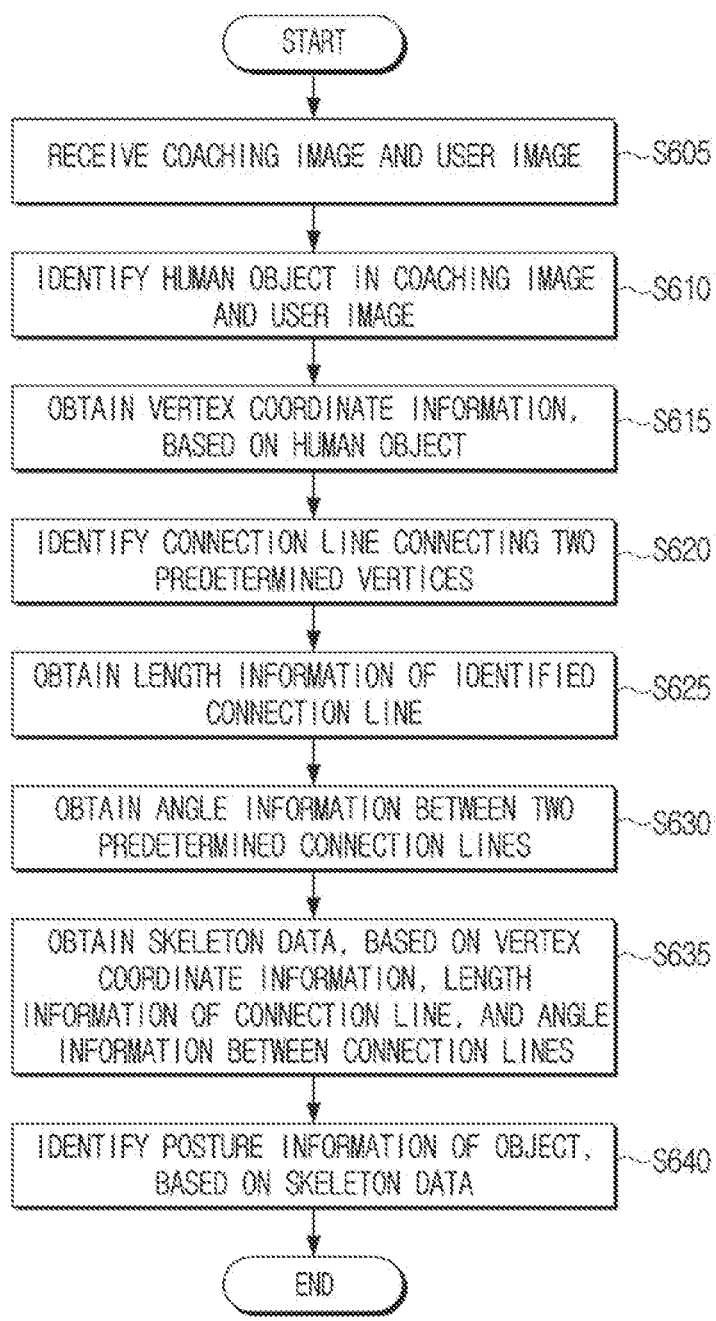
FIG. 6 is a flowchart of a process of obtaining skeleton data.

FIG. 6 is a flowchart of a process of obtaining skeleton data. In FIG. 6, the electronic apparatus 100 may receive a coaching image and a user image (S605). Next, the electronic apparatus 100 may identify a human object in each of the coaching image and the user image (S610). The human object is a human-shaped object and may be understood as a human image or a human-shaped character image. Next, the electronic apparatus 100 may obtain vertex coordinate information based on the human object identified in each of the coaching image and the user image (S615). The term "vertex" may refer to a position of a human skeleton, and may be understood to include positions of the head, chest, shoulders, elbows, wrists, waist, knees, ankles, etc. of a human.

Next, the electronic apparatus 100 may identify a connection line connecting two predetermined connection lines among the plurality of pieces of vertex coordinate information (S620). Next, the electronic apparatus 100 may obtain length information of the identified connection line (S625).

Next, the electronic apparatus 100 may obtain angle information between two predetermined connection lines (S630).

Next, the electronic apparatus 100 may obtain skeleton data of each of the coaching image and the user image, based on the vertex coordinate information, the length information of the connection line, and the angle information between the connection lines (S635). Specifically, the electronic apparatus 100 may obtain first skeleton data corresponding to the coaching image and second skeleton data corresponding to the user image.

Thereafter, the electronic apparatus 100 may identify posture information of each object, based on the obtained first skeleton data and second skeleton data (S640). Specifically, the electronic apparatus 100 may identify posture information of a first object corresponding to the first skeleton data and posture information of a second object corresponding to the second skeleton data.

Figure 7:
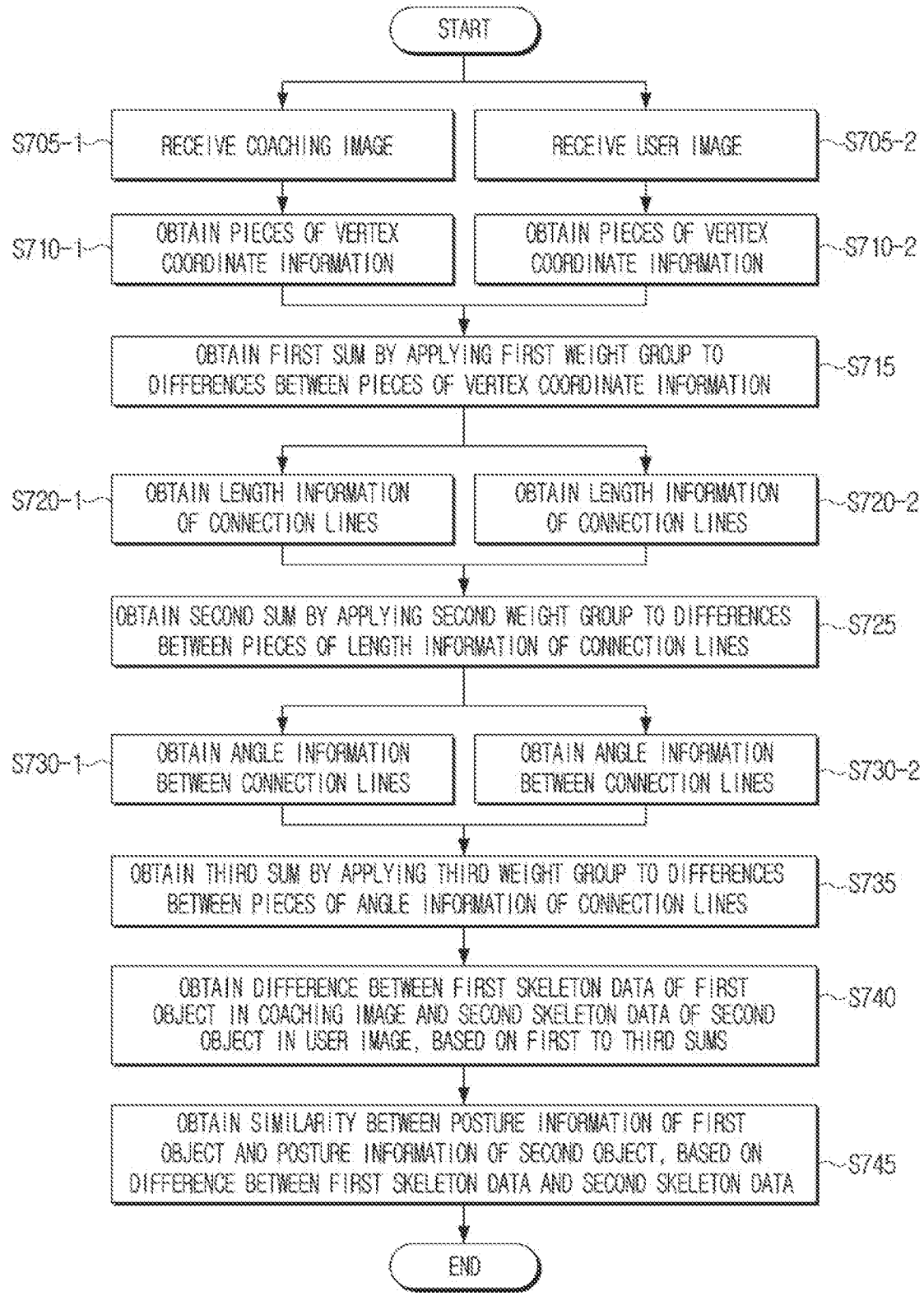
FIG. 7 is a flowchart of a process of obtaining a similarity between pieces of posture information based on skeleton data.

FIG. 7 is a flowchart of a process of obtaining a similarity between pieces of posture information based on skeleton data. In FIG. 7, the electronic apparatus 100 may receive a coaching image (S705-1) and obtain a plurality of pieces of vertex coordinate information from the received coaching image (S710-1).

Next, the electronic apparatus 100 may receive a user image (S705-2) and obtain a plurality of pieces of vertex coordinate information from the received user image (S710-2). The electronic apparatus 100 may obtain a first sum by applying a first weight group to differences between the plurality of pieces of vertex coordinates obtained from the coaching image and the plurality of pieces of vertex coordinate information obtained from the user image (S715). Specifically, the electronic apparatus 100 may obtain differences between the pieces of vertex coordinate information of the coaching image and the pieces of vertex coordinate information of the user image, and multiply each of the obtained differences by the first weight group. Next, the electronic apparatus 100 may obtain the first sum by accumulating values obtained by multiplying the differences by the first weight group.

Next, the electronic apparatus 100 may obtain length information of a plurality of connection lines based on the plurality of pieces of vertex coordinate information included in the coaching image (S720-1). Next, the electronic apparatus 100 may obtain length information of a plurality of connection lines based on the plurality of pieces of vertex coordinate information included in the user image (S720-2). Next, the electronic apparatus 100 may obtain a second sum by applying a second weight group to differences between the length information of the plurality of connection lines included in the coaching image and the length information of the plurality of pieces of connection lines included in the user image (S725).

Next, the electronic apparatus 100 may obtain angle information between the plurality of connection lines included in the coaching image (S730-1). Next, the electronic apparatus 100 may obtain angle information between the plurality of connection lines included in the user image (S730-2). Next, the electronic apparatus 100 may obtain a third sum by applying a third weight group to differences between a plurality of pieces of angle information obtained from the coaching image and a plurality of pieces of angle information obtained from the user image (S735).

Next, the electronic apparatus 100 may obtain a difference between first skeleton data of a first object in the coaching image and second skeleton data of a second object in the user image, based on the first sum obtained in operation S715, the second sum obtained in operation S725, and the third sum obtained in operation S735 (S740).

Thereafter, the electronic apparatus 100 may obtain a similarity between posture information of the first object and posture information of the second object based on a difference between the first skeleton data and the second skeleton data (S745).

The operation for obtaining the difference described above with reference to FIG. 7 may be understood as differences between data of the coaching image and data of the user image corresponding to the data of the coaching image, as will be described in detail with reference to FIG. 8 below.

FIG. 8 is a diagram for describing a process of obtaining a similarity between pieces of posture information based on skeleton data. In FIG. 8, skeleton data of fifteen vertices are identified in a coaching image and a user image to obtain a similarity.

According to a first embodiment 805, the electronic apparatus 100 may obtain differences between a plurality of pieces of vertex coordinate information included in the coaching image and the user image. In order to distinguish between information of the coaching image and information of the user image, the pieces of vertex coordinate information of the coaching image will be described as $Vc1$ to $Vc15$, and the pieces of vertex coordinate information of the user image will be described as $Vu1$ to $Vu15$.

The electronic apparatus 100 may obtain differences between the pieces of vertex coordinate information of the coaching image and the pieces of vertex coordinate information of the user image. Objects between which a difference is calculated may be vertices representing the same position. For example, the electronic apparatus 100 may obtain a difference between pieces of vertex coordinate information $Vc1$ and $Vu1$ in the coaching image and the user image each indicating a position of the neck. The difference may be obtained using the Euclidean distance, and a function symbol thereof may be $E(\ )$. That is, in the coaching image and the user image, a difference $DV(1)$ between first vertices may be expressed as $E(Vc1,Vu1)$, a difference $DV(2)$ between second vertices may be expressed as $E(Vc2, Vu2)$, and a difference $DV(15)$ between fifteenth vertices may be expressed as $E(Vc15,Vu15)$.

Alternatively or additionally, the electronic apparatus 100 may obtain a first sum $DV(total)$ by accumulating values obtained by multiplying the differences $DV(1)$ to $DV(15)$ by a first weight groups $wv1$ to $wv15$. The first sum value $DV(total)$ may be $wv1*DV(1)+ \ldots +wv15*DV(15)$.

According to a second embodiment 810, the electronic apparatus 100 may obtain length information of a connection line connecting vertices. Objects between which a difference is calculated may be connection lines representing the same position. For example, the electronic apparatus 100 may obtain the difference between pieces of length information of the connection lines connecting the first and second vertices in the coaching image and the user image. The difference may be obtained using an absolute difference and a function symbol thereof may be $d(\ )$. That is, in the coaching image and the user image, the difference $DL(1,2)$ between the pieces of the length information of the connection lines connecting the first and second vertices may be expressed as $d(L(Vc1,Vc2), L(Vu1,Vu2))$, a difference $DL(1,3)$ between pieces of length information of connection lines connecting the first and third vertices may be expressed as $d(L(Vc1,Vc3), L(Vu1,Vu3))$, and a difference $DL(14,15)$ between pieces of the length information of connection lines connecting the fourteenth and fifteenth vertices may be expressed as $d(L(Vc14,Vc15), L(Vu14,Vu15))$.

Alternatively or additionally, the electronic apparatus 100 may obtain a second sum $DL(total)$ by accumulating values obtained by multiplying the differences $DL(1,2)$ to $DL(14, 15)$ by a second weight groups $wl1$ to $wl15$. The second sum $(DL(total))$ may be $wl1*DL(1,2)+wl2*DL(1,3)+ \ldots +wl14*DL(14,15)$.

According to a third embodiment 815, the electronic apparatus 100 may obtain a difference between pieces of angle information between connection lines. Objects between which a difference is calculated may be angles representing the same position. For example, the electronic apparatus 100 may obtain the difference between pieces of angle information between the connection lines connecting the first and second vertices in the coaching image and the user image. The difference may be obtained using cosine similarity and a function symbol thereof may be $C(\ )$. That is, in the coaching image and the user image, a difference $DA(1,2-1,3)$ between pieces of angle information between the connection line connecting the first and second vertices and the connection line connecting the first and third vertices may be expressed as $C(A(L(Vc1, Vc2), L(Vc1, Vc3)), A(L(Vu1, Vu2), L(Vu1, Vu3))$, a difference $DA(1,2-1,6)$ between pieces of angle information between the connection line connecting the first and second vertices and the connection line connecting the first and sixth vertices may be expressed as $C(A(L(Vc1, Vc2), L(Vc1, Vc6)), A(L(Vu1,$ Vu2), L(Vu1, Vu6)), and a difference DA(13,14-14,15) between pieces of angle information between the connection line connecting the thirteenth and fourteenth vertices and the connection line connecting the fourteenth and fifteenth vertices may be expressed as C(A(L(Vc13, Vc14), L(Vc14, Vc15)), A(L(Vu13, Vu14), L(Vu14, Vu15)).

Alternatively or additionally, the electronic apparatus 100 may obtain a third sum DA(total) by accumulating values obtained by multiplying the difference values DA(1,2-1,3) to DA(13,14-14,15) by a third weight group wa1 to wa15. The third sum (DA(total)) may be wa1*DA(1,2-1,3)+wa2*DA(1,2-1,6)+ . . . +wa14*DA(13,14-14,15).

According to a fourth embodiment 820, the electronic apparatus 100 may obtain a skeleton data difference D(total) by adding values obtained by multiplying the first sum DV(total) by a first weight w1, the second sum DL(total) by a second weight w2, and the third sum DA(total) by a third weight w3.

Figure 9:
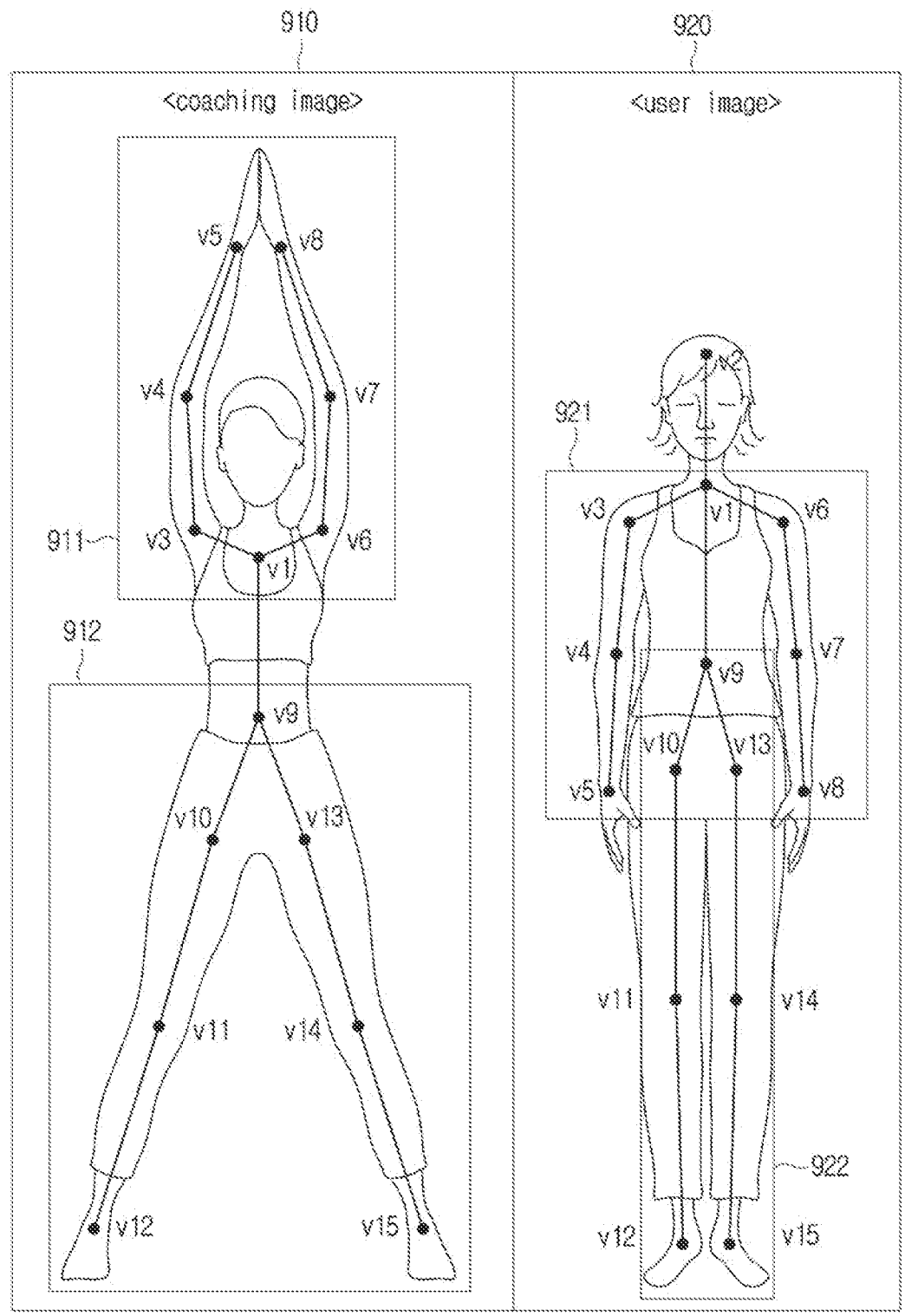
FIG. 9 is a diagram for describing a process of comparing pieces of posture information with each other based on skeleton data.
Figure 11:
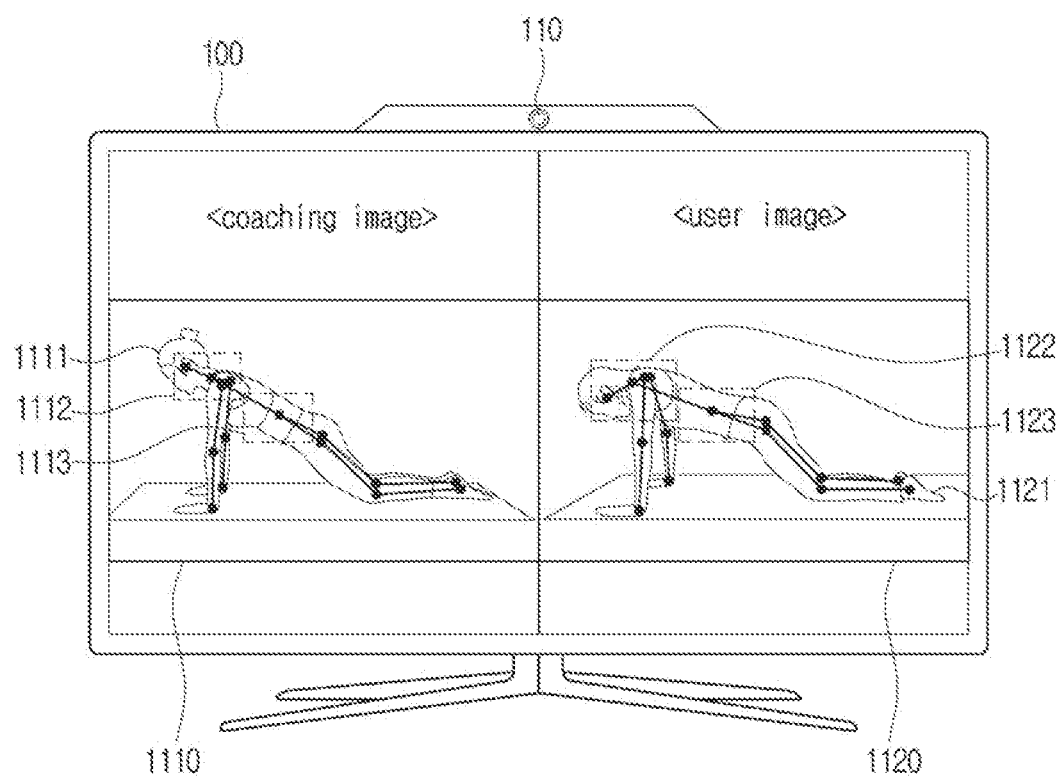
FIG. 11 is a diagram for describing displaying a feedback image according to another embodiment.

Although an operation of obtaining a difference by comparing entire images with each other has been described above with reference to FIG. 8, a specific region in which a difference occurs with respect to vertices as shown in FIGS. 9 and 11.

FIG. 9 is a diagram for describing a process of comparing pieces of posture information with each other based on skeleton data. In FIG. 9, the electronic apparatus 100 may obtain first skeleton data from a coaching image 910 and second skeleton data from a user image 920.

The electronic apparatus 100 may compare the first skeleton data and the second skeleton data with each other to identify regions between which a greatest difference occurs. Specifically, the electronic apparatus 100 may identify that a first region 911 with vertices v1 to v8 in the coaching image and a second region 921 with vertices v1 to v8 in the user image are regions between which a greatest difference occurs. Alternatively or additionally, the electronic apparatus 100 may identify a third region 912 with vertices v9 to v15 in the coaching image and a fourth region 922 with vertices v9 to v15 in the user image.

The electronic apparatus 100 may identify regions between which a greatest difference occurs, based on vertex coordinate information, length information of connection lines, and angle information between connection lines. The electronic apparatus 100 may determine that a difference between the first region 911 and the second region 921 is large and a difference between the third region 912 and the fourth region 922 is large.

For example, the electronic apparatus 100 may identify a region of the coaching image and a region of the user image between which a difference is greatest. The electronic apparatus 100 may obtain a difference by comparing vertices of the coaching image with those of the user image, and identify vertices between which a difference is greater than or equal to a threshold, based on the obtained difference. Alternatively or additionally, the electronic apparatus 100 may identify a region in which a difference greater than or equal to the threshold occurs, based on at least one vertex at which the difference greater than or equal to the threshold occurs. The first region 911, the second region 921, the third region 912, and the fourth region 922 may be described herein as comparison regions. The comparison regions may be understood as regions in which a difference greater than or equal to the threshold occurs.

Figure 10:
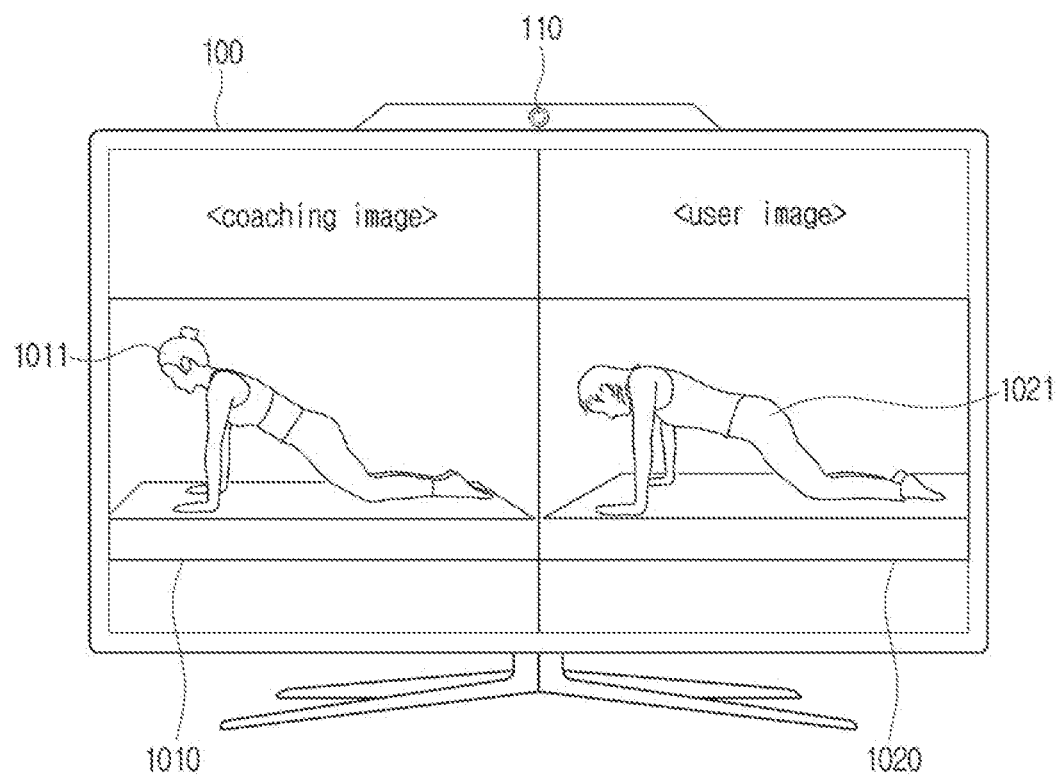
FIG. 10 is a diagram for describing displaying a feedback image according to an embodiment.

FIG. 10 is a diagram for describing displaying a feedback image according to an embodiment. In FIG. 10, the electronic apparatus 100 may photograph a user using the camera 110 and obtain a user image.

The electronic apparatus 100 may analyze the user image to identify whether the user's gaze is not directed to the electronic apparatus 100.

When the user's gaze is not directed to the electronic apparatus 100 (when the user's eyes are turned down), the electronic apparatus 100 may generate a feedback image including a coaching image 1010 and a user image 1020. Thereafter, the electronic apparatus 100 may display the generated feedback image on the display 120.

The electronic apparatus 100 may generate the feedback image such that a human object in the coaching image and a human object in the user image are displayed in the same size.

The size of the human object identified in the coaching image and the size of the human object identified in the user image may be different from each other. For example, a user object may be identified to be large or small according to settings of a lens for capturing an image. Accordingly, the electronic apparatus 100 may change the size of the human object identified in the user image to generate the feedback image. An operation of changing a size of an object will be described with reference to FIG. 21 below.

FIG. 11 is a diagram for describing displaying a feedback image according to another embodiment. In FIG. 11, the electronic apparatus 100 may additionally display a User Interface (UI) 1111 corresponding to first skeleton data in a coaching image 1110 and additionally display UIs 1112 and 1113 for a comparison region. Alternatively or additionally, the electronic apparatus 100 may additionally display a UI 1121 corresponding to second skeleton data in a user image 1120 and additionally display UIs 1122 and 1123 for a comparison region.

According to an embodiment, the electronic apparatus 100 may generate a feedback image by adding the UI 1111 corresponding to the first skeleton data and the UIs 1112 and 1113 for the comparison region to the coaching image 1110 and adding the UI 1121 corresponding to the second skeleton data and the UIs 1121 and 1123 for the comparison region to the user image 1120.

The comparison regions may be understood as regions in which a difference greater than or equal to a threshold occurs.

Figure 12:
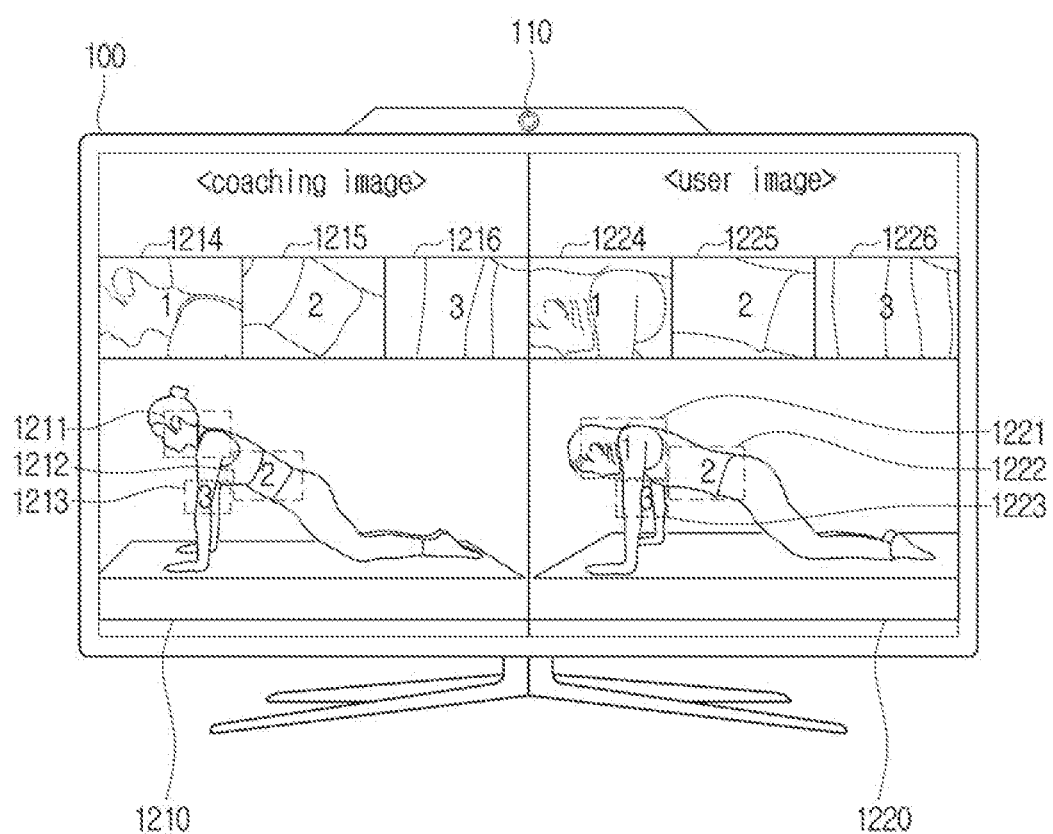
FIG. 12 is a diagram for describing displaying a feedback image according to another embodiment.

FIG. 12 is a diagram for describing displaying a feedback image according to another embodiment. In FIG. 12, the electronic apparatus 100 may generate a sub-image corresponding to a coaching image 1210 and a sub-image corresponding to a user image 1220.

Specifically, the electronic apparatus 100 may identify comparison regions of the coaching image 1210 and the user in the user image 1220. For example, the electronic apparatus 100 may identify comparison regions 1211, 1212, and 1213 in the coaching image 1210 and comparison regions 1221, 1222, and 1223 in the user image 1220.

Alternatively or additionally, the electronic apparatus 100 may obtain a sub-image corresponding to each of these comparison regions. The electronic apparatus 100 may change a size of the sub-image. Because these comparison regions correspond to part of posture information in which a greatest difference occurs and thus a user should enlarge the sub-images corresponding to the comparison regions. Accordingly, the electronic apparatus 100 may increase the sizes of region corresponding to the comparison regions to obtain the enlarged sub-images. Alternatively or additionally, the electronic apparatus 100 may display obtained sub-images 1214, 1215, and 1216 at predetermined positions. Likewise, the electronic apparatus 100 may display obtained sub-images 1224, 1225, and 1226 at predetermined positions.

The electronic apparatus 100 may display the sub-images 1214, 1215, and 1216 corresponding to the comparison regions 1211, 1212, and 1213 at positions adjacent to the coaching image 1210, and the sub-images 1224, 1225 and 1226 corresponding to the comparison regions 1221, 1222, and 1223 at positions adjacent to the user image 1220.

According to an embodiment, the electronic apparatus 100 may generate a feedback image by adding the sub-images 1214, 1215, and 1216 to the coaching image 1210 and the sub-images 1224, 1225, and 1226 to the user image 1220.

Figure 13:
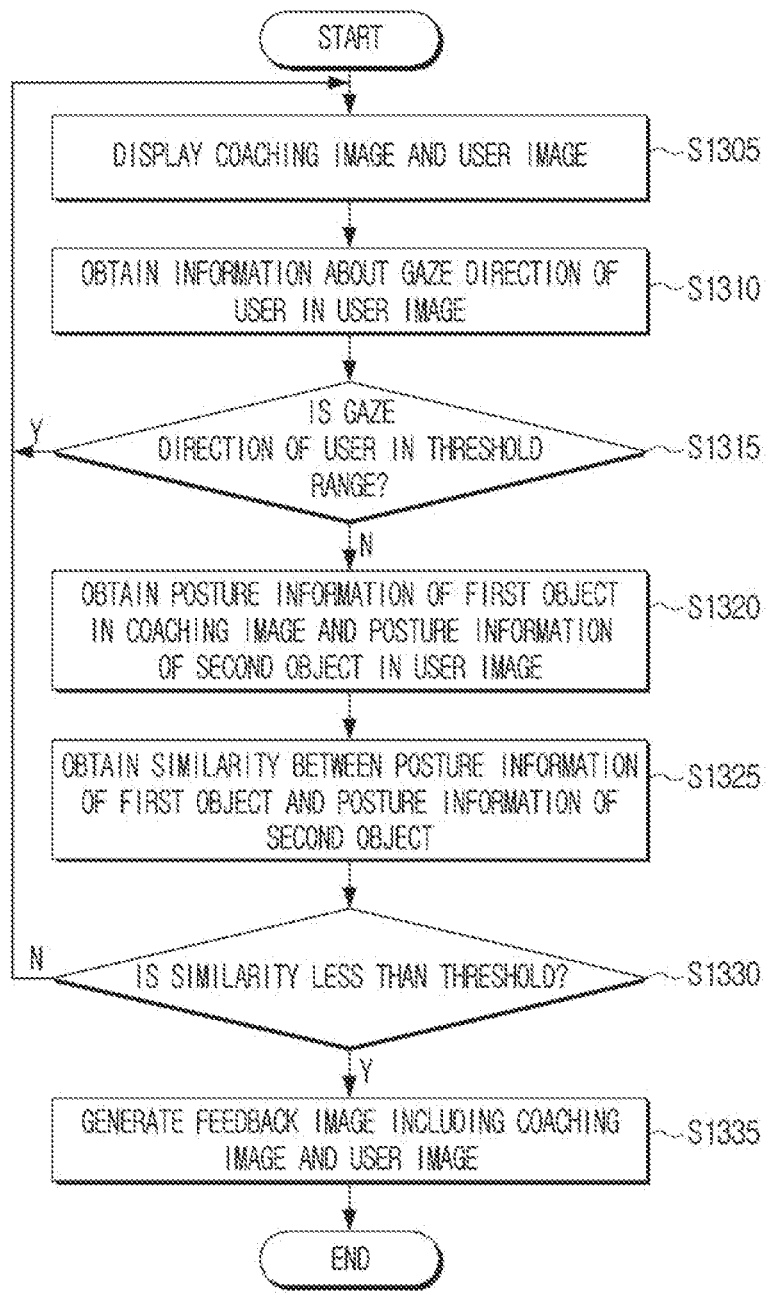
FIG. 13 is a flowchart of generating a feedback image according to an embodiment.

FIG. 13 is a flowchart of generating a feedback image according to an embodiment. In FIG. 13, the electronic apparatus 100 may display a coaching image and a user image on the display 120 (S1305). The electronic apparatus 100 may obtain information about a gaze direction of a user in the user image (S1310).

Next, the electronic apparatus 100 may identify whether the gaze direction of the user is in a threshold range (S1315). The threshold range may be a range in which the user's gaze is directed to the electronic apparatus 100. When the user's gaze is directed to the electronic apparatus 100, the electronic apparatus 100 may identify that the gaze direction of the user is in the threshold range. When the user's gaze is not directed to the electronic apparatus 100, the electronic apparatus 100 may identify that the gaze direction of the user is out of the threshold range. The threshold range may be understood as a value determined in advance in consideration of the gaze direction of the user, and may be changed according to user settings.

When it is identified that the gaze direction of the user is in the threshold range, the electronic apparatus 100 may continuously display the coaching image and the user image on the display 120.

However, when it is identified that the gaze direction of the user is not in the threshold range, the electronic apparatus 100 may obtain posture information of a first object in the coaching image and posture information of a second object in the user image (S1320). The first object and the second object may be understood as human-shaped objects. Next, the electronic apparatus 100 may obtain a similarity between the posture information of the first object and the posture information of the second object (S1325).

Next, the electronic apparatus 100 may determine whether the similarity is less than a threshold (S1330). When the similarity is greater than or equal to the threshold, the electronic apparatus 100 may continuously display the coaching image and the user image on the display 120. However, when the similarity is less than the threshold, the electronic apparatus 100 may generate a feedback image including the coaching image and the user image (S1335).

Figure 14:
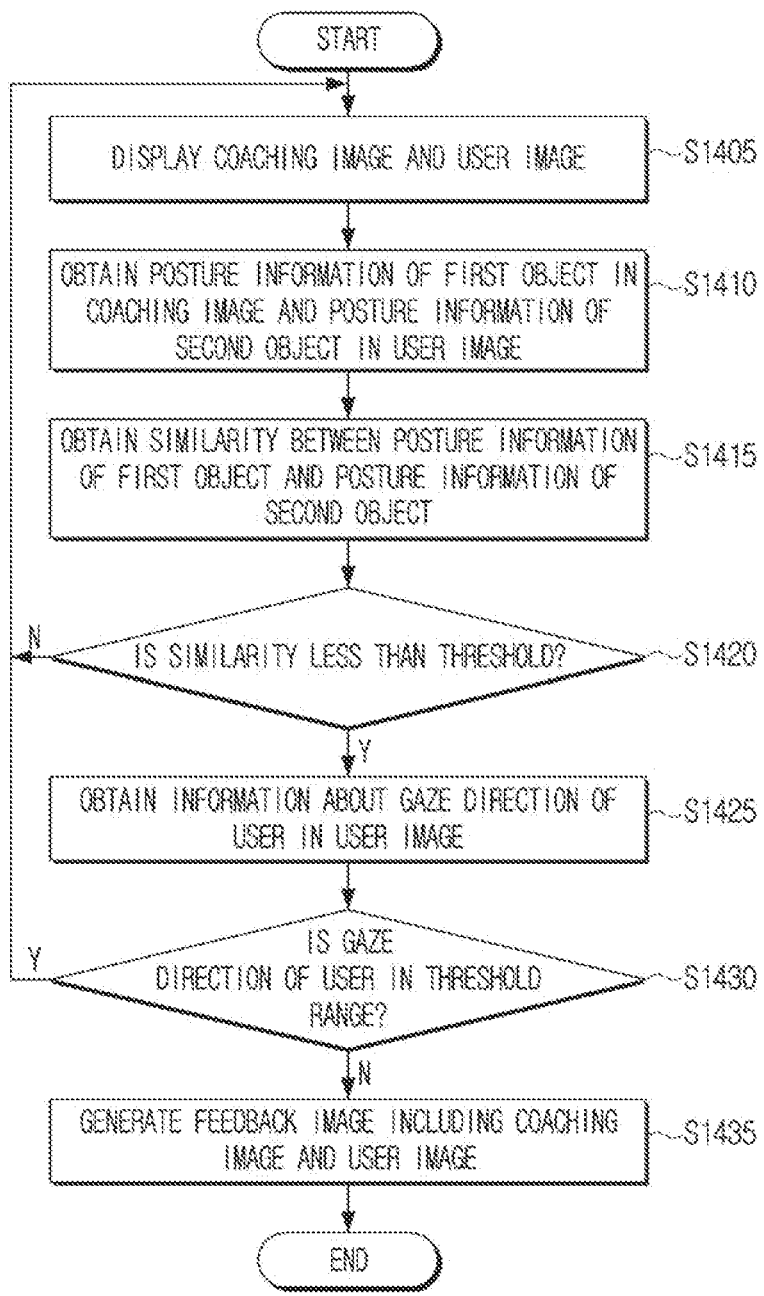
FIG. 14 is a flowchart of generating a feedback image according to another embodiment.

FIG. 14 is a flowchart of generating a feedback image according to another embodiment. In FIG. 14, the electronic apparatus 100 may display a coaching image and a user image on the display 120 (S1405).

Next, the electronic apparatus 100 may directly obtain posture information of a first object from the coaching image and posture information of a second object from the user image (S1410). Next, the electronic apparatus 100 may obtain a similarity between the posture information of the first object and the posture information of the second object (S1415).

Next, the electronic apparatus 100 may determine whether the similarity is less than a threshold (S1420). When the similarity is greater than or equal to the threshold, the electronic apparatus 100 may continuously display the coaching image and the user image on the display 120. However, when the similarity is less than the threshold, the electronic apparatus 100 may obtain information about a gaze direction of a user from the user image (S1425).

Next, the electronic apparatus 100 may identify whether the gaze direction of the user is in a threshold range (S1430). When it is identified that the gaze direction of the user is in the threshold range, the electronic apparatus 100 may continuously display the coaching image and the user image on the display 120. However, when it is identified that the gaze direction of the user is not in the threshold range, the electronic apparatus 100 may generate a feedback image including the coaching image and the user image (S1435).

In the embodiment of FIG. 13, a gaze direction of a user is determined and thereafter a similarity between pieces of posture information is determined, whereas in the embodiment of FIG. 14, a similarity between pieces of posture information is determined and thereafter a gaze direction of a user is determined.

In the embodiment of FIG. 13, data throughput may be less than that of FIG. 14, because a similarity between pieces of posture information is not determined when the gaze direction of the user is in the threshold range. Accordingly, a processing speed in the embodiment of FIG. 13 may be very high.

In the embodiment of FIG. 14, all similarities between pieces of posture information may be compared with each other regardless of the gaze direction of the user. Accordingly, all images with a similarity of less than a threshold may be obtained according to the user's setting, and a feedback image may be generated by extracting a corresponding image only when the gaze direction of the user is not in the threshold range. The electronic apparatus 100 may give greater importance to the calculation of similarity than the gaze direction of the user to improve the quality of the feedback image.

Figure 15:
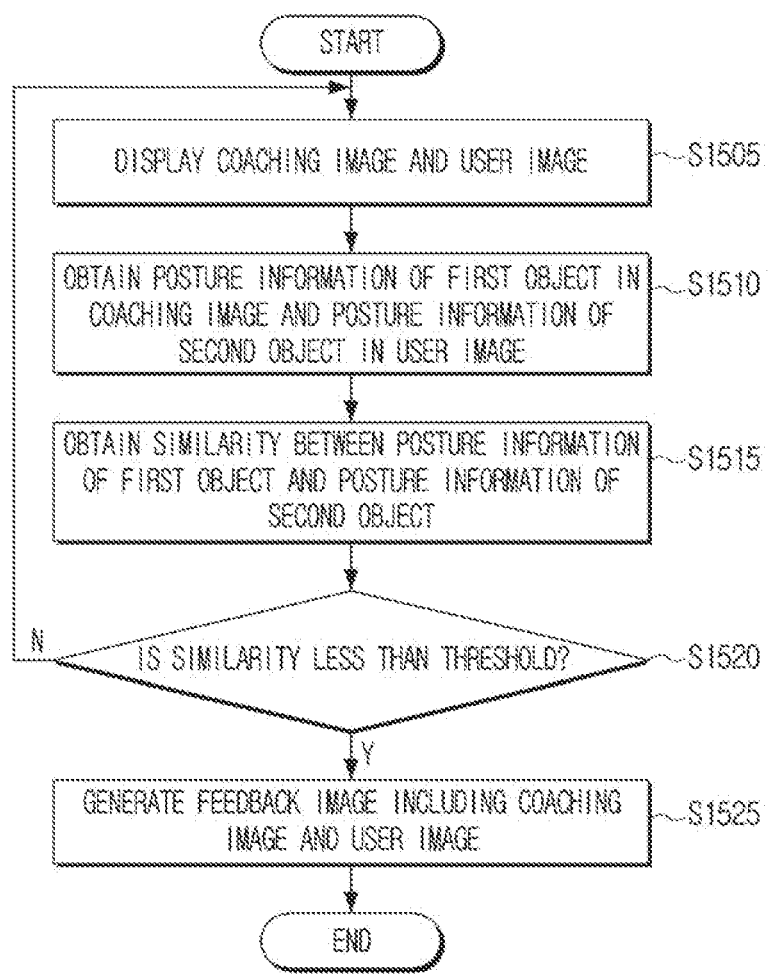
FIG. 15 is a flowchart of generating a feedback image according to another embodiment.

FIG. 15 is a flowchart of generating a feedback image according to another embodiment. In FIG. 15, operations S1505, S1510, S1515, and S1520 may correspond to operations S1405, S1410, S1415, and S1420 of FIG. 14.

When an obtained similarity is greater than or equal to a threshold, the electronic apparatus 100 may continuously display a coaching image and to user image on the display 120.

However, when the similarity is less than the threshold, the electronic apparatus 100 may generate a feedback image including the coaching image and the user image (S1525).

However, in the embodiment of FIG. 15, a gaze direction of a user is not taken into account, all motions of the user who take a posture different from that in the coaching image may be included in the feedback image.

Figure 16:
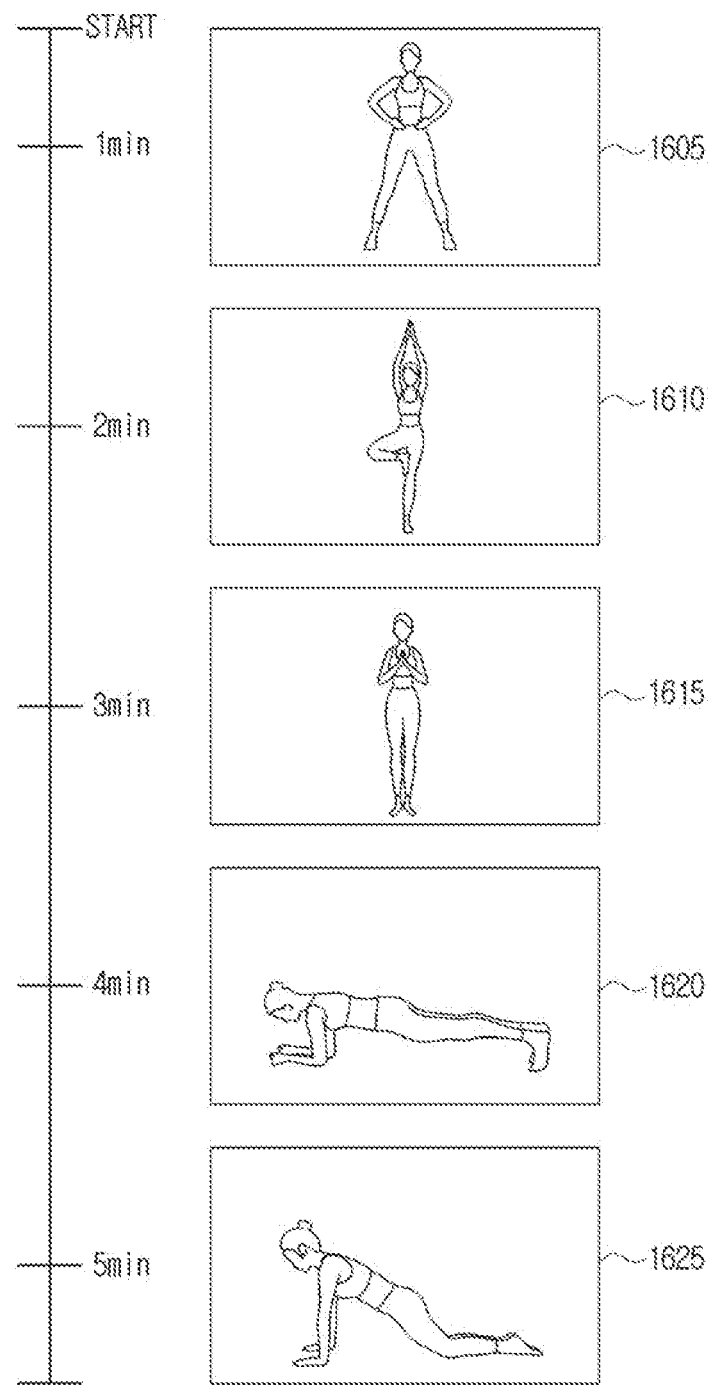
FIG. 16 is a diagram for describing a process of including only some of received user images in a feedback image.

FIG. 16 is a diagram for describing a process of including only some of received user images in a feedback image. In FIG. 16, the electronic apparatus 100 may identify a gaze direction of a user, i.e., a human object (second object) included in a user image. Alternatively or additionally, a feedback image may be generated only when the identified gaze direction of the user is not in a threshold range.

According to the embodiment of FIG. 16, the electronic apparatus 100 may identify that a gaze direction of a user is directed to the electronic apparatus 100, based on a user image 1605 displayed at a one-minute time point and a user image 1610 displayed at a two-minute time point.

The electronic apparatus 100 may identify that the gaze direction of the user is not directed to the electronic apparatus 100, based on a user image 1615 displayed at a three-minute time point.

Alternatively or additionally, the electronic apparatus 100 may identify that the gaze direction of the user is not directed to the electronic apparatus 100, based on a user image 1620 displayed at a four-minute time point and a user image 1625 displayed at a five-minute time point.

The electronic apparatus 100 may generate a feedback image in a period (three-minute time point to five-minute time point) corresponding to points in time when the gaze direction of the user is not directed to the electronic apparatus 100. Only the user images 1615, 1620 and 1625 respectively displayed at the three-minute time point, the four-minute time point and the five-minute time point, when the gaze direction of the user is not directed to the electronic apparatus 100, may be included in the feedback image.

The electronic apparatus 100 may identify the user image 1615, which is displayed at the three-minute time point, as a predetermined posture (bowing position) and thus exclude the user image 1610 from the feedback image.

Figure 17:
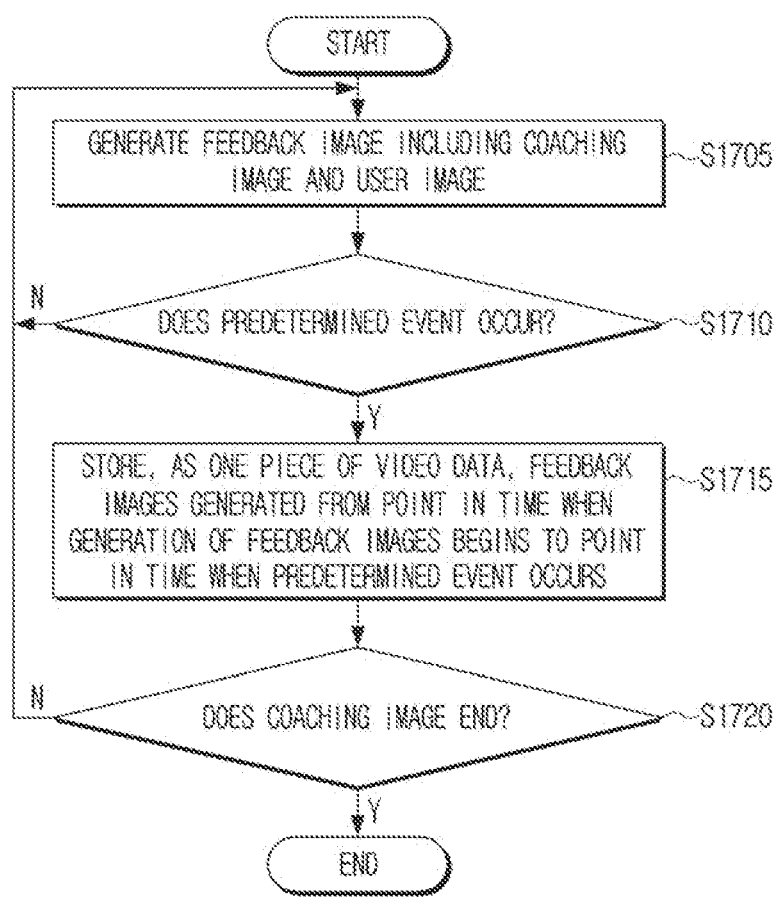
FIG. 17 is a flowchart of identifying feedback images.

FIG. 17 is a flowchart of identifying feedback images. In FIG. 17, the electronic apparatus 100 may generate a feedback image including a coaching image and a user image (S1705). Operation S1705 may be understood as including all of the operations of FIGS. 13 to 15.

The electronic apparatus 100 may identify whether a predetermined event has occurred (S1710). The predetermined event may include at least one of an event in which a human object included in a user image is identified as taking a predetermined posture, an event in which scenes of a coaching image are changed, an event in which a place included in the coaching image is changed to another place, or an event in which predetermined voice (e.g., "next") is output.

When the determined event does not occur, the electronic apparatus 100 may repeatedly generate a feedback image. However, when the predetermined event occurs, the electronic apparatus 100 may store, as a piece of video data, feedback images generated from a point in time when generation of the feedback images begins to a point in time when the predetermined event occurs (S1715).

The predetermined event may be a criterion for dividing the feedback images. For example, the predetermined event is a bowing posture. In general, new content may be displayed when the bowing posture is taken. Thus, whenever the bowing posture is displayed in a coaching images, feedback images may be additionally grouped. That is, when operation 1715 of FIG. 17 is omitted, a video may be stored in one-hour coaching images but two or more videos may be stored with respect to the one-hour coaching images through operation S1715. When a video is stored by dividing it into several parts, there is an advantage that a user can easily edit or watch each of the parts of the video divided according to a specific criterion.

Thereafter, the electronic apparatus 100 may determine whether the coaching image ends (S1720). When it is determined that the coaching image does not end, the electronic apparatus 100 may repeatedly perform operations S1705, S1710, and S1715. However, when it is determined that the coaching image ends, the electronic apparatus 100 may end the generation of the feedback image.

Figure 18:
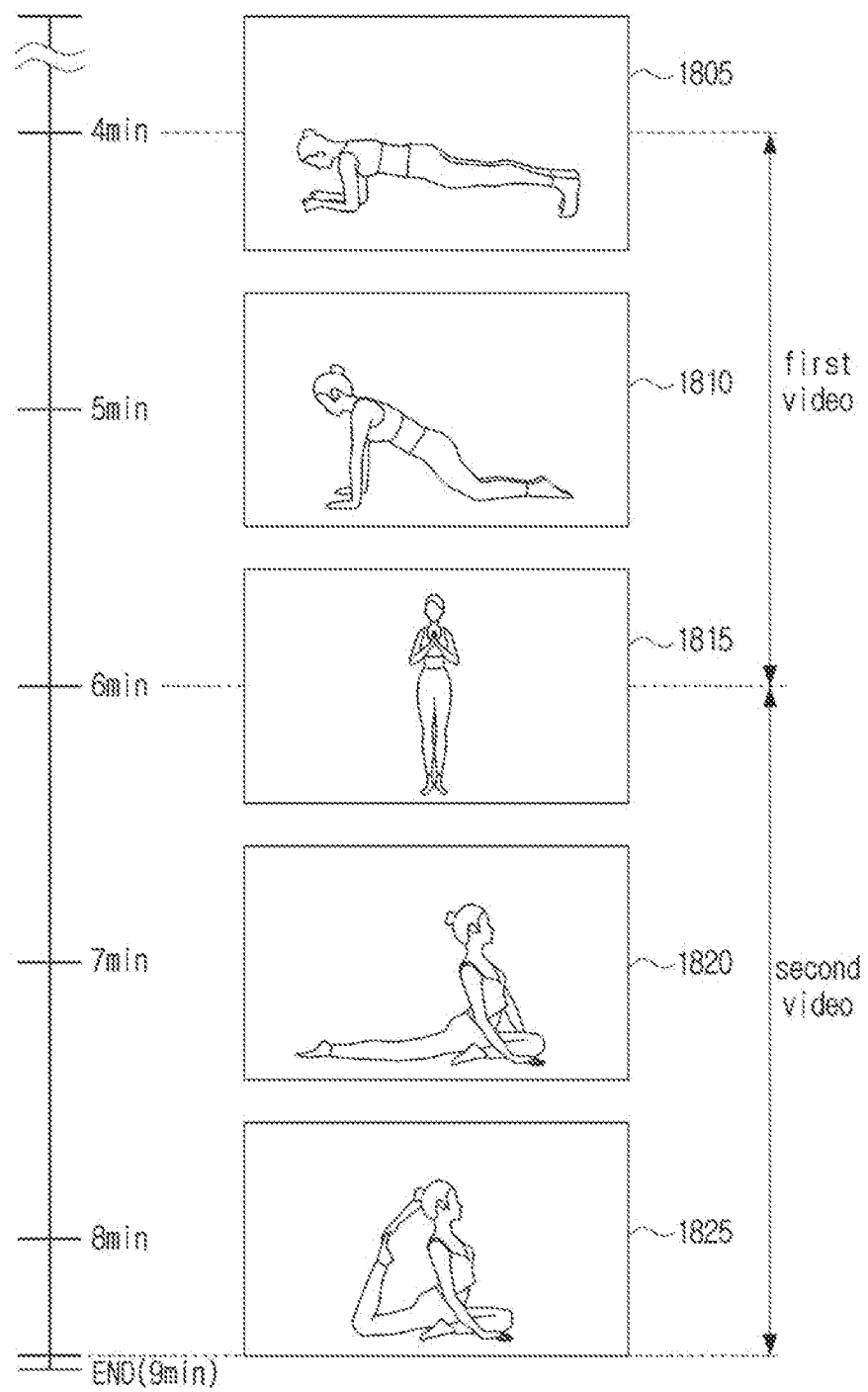
FIG. 18 is a diagram for describing identifying feedback images.

FIG. 18 is a diagram for describing identifying feedback images. In FIG. 18, the electronic apparatus 100 may identify that a gaze direction of a user is not directed to the electronic apparatus 100 in all a user image 1805 displayed at a four-minute time point, a user image 1810 displayed at a five-minute time point, a user image 1815 displayed at a six-minute time point, a user image 1820 displayed at a seven-minute time point, and a user image 1825 displayed at an eight-minute time point.

Accordingly, the electronic apparatus 100 may generate feedback images in a time period (four-minute time point to nine-minute time point) corresponding to points in time when the user images 1805, 1810, 1815, 1820, and 1825 are displayed.

According to an embodiment, the electronic apparatus 100 may generate a piece of video data by synthesizing feedback images generated in the time period (four-minute time point to nine-minute time point) corresponding to points in time when the user images 1805, 1810, 1815, 1820, and 1825 are displayed, and store the piece of video data in the memory 130.

According to another embodiment, the electronic apparatus 100 may further identify whether a predetermined event has occurred in the time period (four-minute time point to nine-minute time point) corresponding to the points in time when the user image 1805, 1810, 1815, 1820, and 1825 are displayed. The predetermined event may be understood as an event in which a predetermined posture (e.g., a bowing posture) of a first object included in a coaching image is identified. According to an embodiment, the predetermined event may include an event in which the coaching image ends in addition to the event in which the predetermined posture of the first object is identified.

The user image 1815 displayed at the six-minute time point is an image in which the predetermined posture of the first object is identified. Accordingly, the electronic apparatus 100 may divide videos with respect to the six-minute time point as a criterion. For example, the electronic apparatus 100 may generate a video (first video) based on feedback images generated from the point in time when the generation of the feedback images begins (four-minute time point) to the point in time when the predetermined event is identified (six-minute time point). Alternatively or additionally, the electronic apparatus 100 may generate a video (second video) based on feedback images generated from the point in time when the predetermined event is identified (six-minute time point) to the point in time when the predetermined event is identified again or the coaching image ends (nine-minute time point).

The electronic apparatus 100 may store the generated first and second videos in the memory 130.

Figure 19:
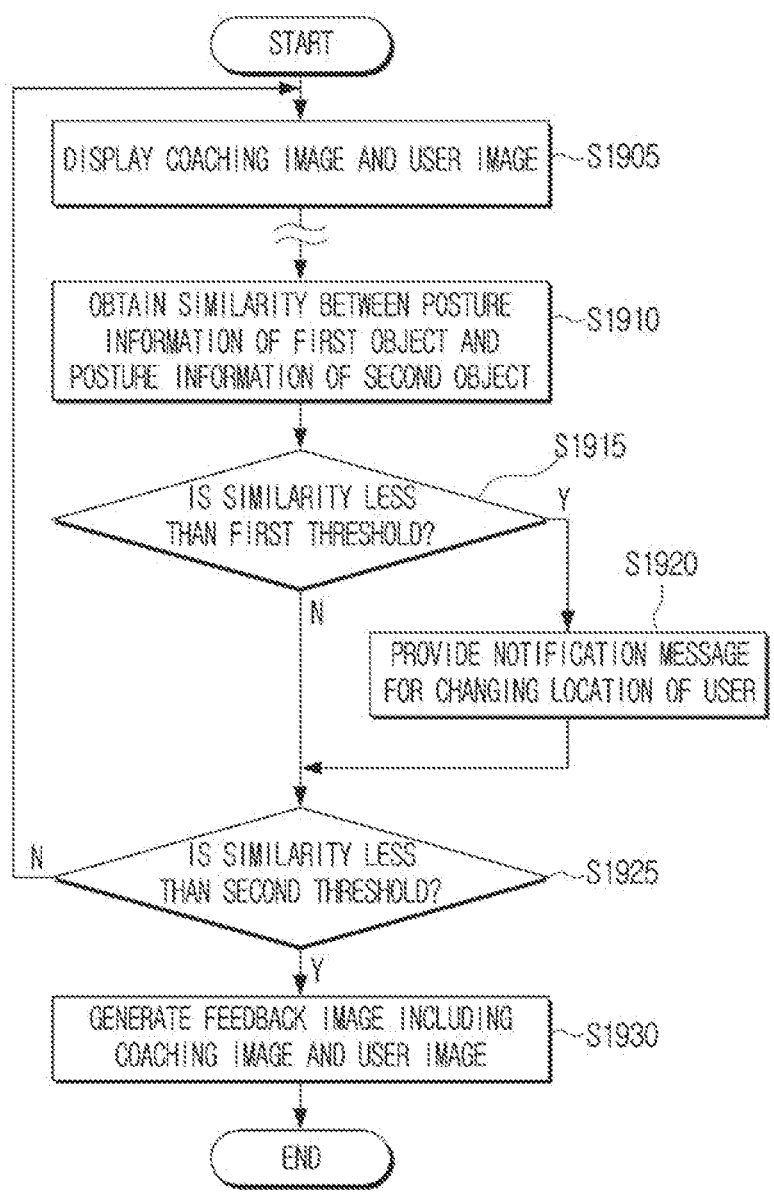
FIG. 19 is a flowchart of providing a notification message for changing a location of a user.

FIG. 19 is a flowchart of providing a notification message for changing a location of a user. In FIG. 19, the electronic apparatus 100 may receive a coaching image and a user image (S1905). Next, the electronic apparatus 100 may obtain posture information of a first object and posture information of a second object (S1910). Operations S1905 and S1910 may be a concept including operations S1305, S1310, S1315, S1320, and S1325.

The electronic apparatus 100 may determine whether a similarity is less than a first threshold (S1915). When the similarity is less than the first threshold, the electronic apparatus 100 may provide a user with a notification message to change a location of the user (S1920).

When the electronic apparatus 100 directly photographs the user by the camera 110, an automatic user tracking function may be additionally used. However, in an embodiment in which the automatic user tracking function is not used, the electronic apparatus 100 should provide the user with information indicating that the user is not recognized within an imaging range. This is because the coaching image and the user image cannot be accurately compared with each other.

When the user is completely out of the imaging range, the similarity may be a very small value. Thus, when it is identified that the similarity is less than the first threshold, it may be determined that the user is at least partially out of the imaging range and thus a notification message may be provided to the user. A concrete example of the notification message will be described with reference to FIG. 20 below.

However, when the similarity is greater than or equal to the first threshold, the electronic apparatus 100 may determine whether the similarity is less than a second threshold (S1925). When the similarity is greater than or equal to the second threshold, the electronic apparatus 100 may repeatedly perform operations S1905 to S1915. However, when the similarity is less than the second threshold, the electronic apparatus 100 may generate a feedback image including the coaching image and the user image (S1930).

Figure 20:
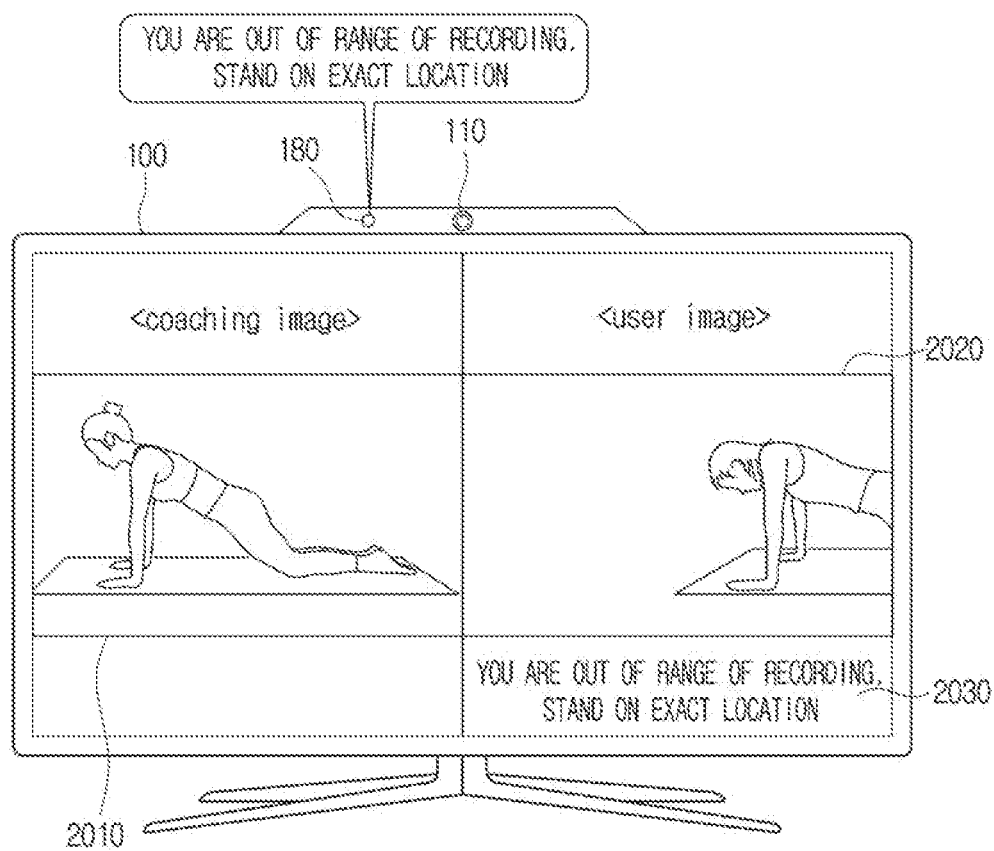

FIG. 20 is a diagram for describing providing a notification message for changing a location of a user. In FIG. 20, the electronic apparatus 100 may display a notification message of image data on the display 120 and output a notification message of audio data through the speaker 180. The electronic apparatus 100 may provide a user with a notification message of at least one of an image data form or an audio data form.

The electronic apparatus 100 may display a UI 2030 corresponding to the notification message near a location at which user images are displayed. When coaching images are displayed in real time, the UI 2030 may be displayed in an area in which coaching images and user images are not displayed not to interrupt watching the coaching images.

Figure 21:
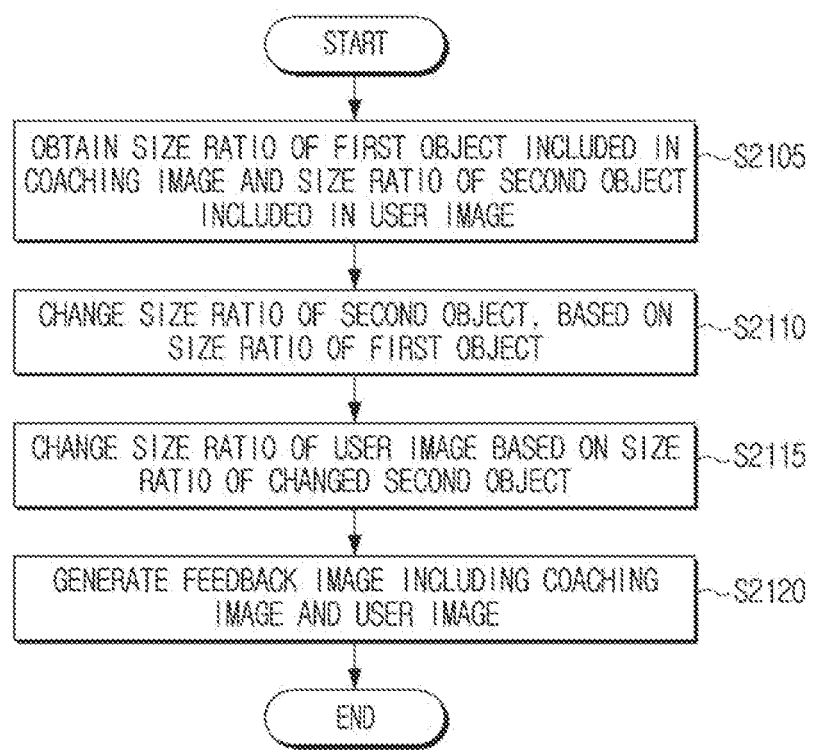
FIG. 21 is a flowchart of generating a feedback image by changing a size of a user image.

FIG. 21 is a flowchart of generating a feedback image by changing a size of a user image. In FIG. 21, the electronic apparatus 100 may obtain a size ratio of a first object included in a coaching image and a size ratio of a second object included in a user image (S2105). Specifically, the electronic apparatus 100 may identify the size of a human object included in each image.

Next, the electronic apparatus 100 may change the size ratio of the second object based on the size ratio of the first object (S2110). For example, the first object is displayed at a ratio of 40% in the entire coaching image and the second object is displayed at a ratio of 60% in the entire user image. The electronic apparatus 100 may change the size ratio of the second object from 60% to 40%.

Because a feedback image is generated to compare the coaching image with the user image, size ratios of objects should also be the same. Accordingly, the electronic apparatus 100 may change the size ratio of the second object in the user image based on the size ratio of the first object in the coaching image (S2115).

The electronic apparatus 100 may modify the user image to change the size ratio of the second object. To increase the size ratio of the second object, the electronic apparatus 100 may modify a certain region of an obtained user image to be expanded. To reduce the size ratio of the second object, the electronic apparatus 100 may reduce the size of the user image.

According to an embodiment, the electronic apparatus 100 may change the setting of the camera 110 so that the size ratio of the second object may be changed without modifying an already obtained image.

The processor 140 may generate a feedback image including the coaching image and the changed user image (S2120).

FIG. 22 is a diagram for describing a method of an electronic apparatus according to an embodiment of the disclosure. In FIG. 22, a method of an electronic apparatus according to an embodiment of the disclosure includes displaying a coaching image and a user image (S2205), identifying a gaze direction of a user based on the user image (S2210), obtaining a feedback image including the coaching image and the user image based on posture information of a first object in the coaching image and posture information of a second object in the user image and storing the obtained feedback image, when the gaze direction of the user is not in a threshold range (S2215), and displaying the stored feedback image (S2220).

The method may further include obtaining a similarity between the posture information of the first object and the posture information of the second object, and obtaining the feedback image including the coaching image and the user image when the similarity is less than a threshold.

The obtaining of the similarity may include obtaining first skeleton data corresponding to the first object based on the obtained coaching image, obtaining second skeleton data corresponding to the second object based on the obtained user image, and obtaining a similarity between the posture information of the first object and the posture information of the second object based on a difference between the first skeleton data and the second skeleton data.

The first skeleton data and the second skeleton data may include vertex coordinate information, length information of connection lines connecting two adjacent vertices, and angle information between two adjacent connection lines, and the obtaining of the similarity may include obtaining a difference between the first skeleton data and the second skeleton data based on the vertex coordinate information, the length information, and the angle information.

The obtaining of the similarity may include applying a first weight group to differences between vertex coordinate information in the first skeleton data and vertex coordinate information in the second skeleton data, obtaining a first sum of the differences to which weights are applied, applying a second weight group to differences between length information of connection lines in the first skeleton data and length information of connection lines in the second skeleton data, obtaining a second sum of the differences to which weights are applied, applying a third weight group to differences between angle information in the first skeleton data and angle information in the second skeleton data, obtaining a third sum of the differences to which weights are applied, and obtaining a difference between the first skeleton data and the second skeleton data based on the first to third sums.

The first weight group, the second weight group, and the third weight group may include different weights.

The obtaining of the similarity may include determining weights included in the first weight group, the second weight group, and the third weight group based on the posture information of the first object.

In the storing of the obtained feedback image (S2220), when the posture information of the first object is identified as a predetermined posture, feedback images from a point in time when generation of the feedback images begins to a first point in time when the predetermined posture is identified may be stored together as a first video, and when a subsequent posture of the identified first object is identified as the predetermined posture, feedback images from the first point in time to a point in time when the predetermined posture is identified again may be stored together as a second video.

The method may further include identifying a sub-region in which a difference between the posture information of the first object and the posture information of the second object is greater than or equal to a threshold, obtaining a sub-image of the coaching image and a sub-image of the user image by changing the sizes of the first object and the second object in the identified sub-region, and generating a feedback image including all the coaching images and all the user images and the obtained sub-images of the coaching image and the user image.

In the identifying of the gaze direction of the user (S2210), a face region corresponding to the second object in the user image may be identified, a face rotation angle may be obtained based on the identified face region, and the gaze direction of the user may be identified based on the face rotation angle.

The method of the electronic apparatus 100 as shown in FIG. 22 may be performed by the electronic apparatus 100 having the configuration of FIG. 1 or 2 and the electronic apparatus 100 having a different configuration.

The methods according to the one or more embodiments of the disclosure described above may be implemented in the form of an application installable in existing electronic apparatuses.

The methods according to the one or more embodiments of the disclosure may be implemented only by upgrading software or hardware for existing electronic apparatuses.

Alternatively or additionally, the one or more embodiments of the disclosure may be implemented by a server embedded in an electronic apparatus or an external server of at least one of the electronic apparatus or a display device.

In an embodiment of the disclosure, the one or more embodiments described above may be embodied as software including instructions stored in a machine (e.g., a computer)-readable storage media. The machine is a device capable of calling an instruction stored in a storage medium and operating according to the called instruction and may include an electronic apparatus according to the embodiments set forth herein. When the instructions are executed by a processor, functions corresponding to the instructions may be performed directly by the processor or under the control of the processor. The instructions may include code generated or executed by a compiler or an interpreter. The machine-readable storage medium may be provided in the form of a non-transitory storage medium. The term "non-temporary" means that the storage medium does not include a signal and is tangible but does not indicate whether data is stored in the storage medium semi-permanently or temporarily.

In one embodiment of the disclosure, the methods according to the one or more embodiments described above may be provided in a computer program product. The computer program product may be traded as a product between a seller and a purchaser. The computer program product may be distributed in the form of a machine-readable storage medium (e.g., a compact disc read-only memory (CD-ROM)) or distributed online via an application store (e.g., PlayStore™). At least a portion of the computer program product when distributed online may be at least temporarily stored in a storage medium such as a memory of a server of a manufacturer, a server of an application store, or a relay server, or may be temporarily generated.

Alternatively or additionally, each component (e.g., a module or a program) according to the above-described one or more embodiments may include a single entity or a plurality of entities, and some of the sub-components described above may be omitted or other sub-components may be further included in the one or more embodiments. Alternatively or additionally, some components (e.g., modules or programs) may be integrated into one entity to perform functions, which are performed by the components prior to the integration, in the same or similar manner. Operations performed by a module, a program, or another component according to one or more embodiments may be performed in a sequential, parallel, iterative, or heuristic manner, at least some of the operations may be executed in a different order or omitted, or other operations may be added.

While the embodiments of the disclosure have been illustrated and described herein, the disclosure is not limited thereto and various modifications may be made therein by those of ordinary skill in the art without departing from the gist of the disclosure as claimed in the accompanying claims and such modifications should not be understood separately from the scope and spirit of the disclosure.

What is claimed is:

1. An electronic apparatus comprising:
a camera;
a display;
a memory; and
a processor configured to:
control the display to display a coaching image received from an external server and a user image obtained through the camera;
identify a gaze direction of a user based on the obtained user image;
when the identified gaze direction of the user is not in a threshold range, obtain a feedback image based on first posture information of a first object included in the coaching image and second posture information of a second object included in the user image, and store the obtained feedback image in the memory; and
control the display to display the stored feedback image,
wherein the feedback signal includes both of the coaching image and the user image, and
wherein the coaching image corresponds to an expert's image for home training or a lecture image related to a type of exercise.

2. The electronic apparatus of claim 1, wherein the processor is further configured to:
obtain a similarity between the first posture information of the first object and the second posture information of the second object; and
based on the obtained similarity being less than a threshold, obtain the feedback image including the coaching image and the user image.

3. The electronic apparatus of claim 2, wherein the processor is further configured to:
obtain first skeleton data corresponding to the first object based on the obtained coaching image;
obtain second skeleton data corresponding to the second object on the obtained user image; and
obtain the similarity between the first posture information of the first object and the second posture information of the second object based on a difference between the first skeleton data and the second skeleton data.

4. The electronic apparatus of claim 3, wherein each of the first skeleton data and the second skeleton data comprises vertex coordinate information, length information of connection lines connecting two adjacent vertices, and angle information between two adjacent connection lines, and
wherein the processor is further configured to obtain the difference between the first skeleton data and the second skeleton data based on the vertex coordinate information, the length information of the connection lines, and the angle information.

5. The electronic apparatus of claim 4, wherein the processor is further configured to:
apply a first weight group to differences between the vertex coordinate information included in the first skeleton data and the vertex coordinate information included in the second skeleton data, and obtain a first sum of the differences to which the first weight group is applied;
apply a second weight group to differences between the length information of the connection lines included in the first skeleton data and the length information of the connection lines included in the second skeleton data, and obtain a second sum of the differences to which the second weight group is applied;
apply a third weight group to differences between the angle information included in the first skeleton data and the angle information included in the second skeleton data, and obtain a third sum of the differences to which the third weight group is applied; and
obtain the difference between the first skeleton data and the second skeleton data based on the first sum, the second sum, and the third sum.

6. The electronic apparatus of claim 5, wherein the first weight group, the second weight group, and the third weight group comprise different weights.

7. The electronic apparatus of claim 5, wherein the processor is further configured to determine weights included in each of the first weight group, the second weight group, and the third weight group based on the first posture information of the first object.

8. The electronic apparatus of claim 1, wherein the processor is further configured to:
based on the first posture information of the first object being identified as a predetermined posture, store, as a first video, feedback images from a time point at which generation of the feedback images begins to a first time point at which the predetermined posture is identified; and
based on a subsequent posture of the identified first object being identified again as the predetermined posture, store, as a second video, feedback images from the first time point to a second time point at which the predetermined posture is identified again.

9. The electronic apparatus of claim 1, wherein the processor is further configured to:
identify a sub-region in which a difference between the first posture information of the first object and the second posture information of the second object is greater than or equal to a threshold;
obtain a sub-image of the coaching image and a sub-image of the user image by changing sizes of the first object and the second object that are included in the identified sub-region; and
generate a feedback image including the coaching image, the user image, the sub-image of the coaching image, and the sub-image of the user image.

10. The electronic apparatus of claim 1, wherein the processor is further configured to:
identify a face region corresponding to the second object included in the user image;
obtain a face rotation angle based on the identified face region; and
identify the gaze direction of the user based on the face rotation angle.

11. A method performed by an electronic apparatus, the method comprising:
displaying a coaching image and a user image;
identifying a gaze direction of a user based on the user image;
when the identified gaze direction of the user is not in a threshold range, obtaining a feedback image based on first posture information of a first object included in the coaching image and second posture information of a second object included in the user image, and storing the obtained feedback image; and
displaying the stored feedback image,
wherein the feedback signal includes both of the coaching image and the user image, and
wherein the coaching image corresponds to an expert's image for home training or a lecture image related to a type of exercise.

12. The method of claim 11, further comprising:
obtaining a similarity between the first posture information of the first object and the second posture information of the second object; and
based on the obtained similarity being less than a threshold, obtaining the feedback image including the coaching image and the user image.

13. The method of claim 12, wherein the obtaining the similarity comprises:
obtaining first skeleton data corresponding to the first object based on the obtained coaching image;
obtaining second skeleton data corresponding to the second object on the obtained user image; and
obtaining the similarity between the first posture information of the first object and the second posture information of the second object based on a difference between the first skeleton data and the second skeleton data.

14. The method of claim 13, wherein each of the first skeleton data and the second skeleton data comprises vertex coordinate information, length information of connection lines connecting two adjacent vertices, and angle information between two adjacent connection lines, and
the obtaining the similarity comprises obtaining the difference between the first skeleton data and the second skeleton data based on the vertex coordinate information, the length information of the connection lines, and the angle information.

15. The method of claim 14, wherein the obtaining the similarity further comprises:
applying a first weight group to differences between the vertex coordinate information included in the first skeleton data and the vertex coordinate information included in the second skeleton data, and obtaining a first sum of the differences to which the first weight group is applied;
applying a second weight group to differences between the length information of the connection lines included in the first skeleton data and the length information of the connection lines included in the second skeleton data, and obtaining a second sum of the differences to which the second weight group is applied;
applying a third weight group to differences between the angle information included in the first skeleton data and the angle information included in the second skeleton data, and obtaining a third sum of the differences to which the third weight group is applied; and obtaining the difference between the first skeleton data and the second skeleton data based on the first sum, the second sum, and the third sum.

* * * * *